United States Patent
Dorsey et al.

(10) Patent No.: US 10,941,452 B2
(45) Date of Patent: Mar. 9, 2021

(54) COMPOSITIONS AND METHODS FOR ISOLATION OF CIRCULATING TUMOR CELLS (CTC)

(71) Applicant: The Trustees of the University of Pennsylvania, Philadelphia, PA (US)

(72) Inventors: Jay F. Dorsey, Media, PA (US); Gary D. Kao, Wynnewood, PA (US); Stephen M. Hahn, Glen Mills, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 15/517,143

(22) PCT Filed: Oct. 5, 2015

(86) PCT No.: PCT/US2015/053982
§ 371 (c)(1),
(2) Date: Apr. 5, 2017

(87) PCT Pub. No.: WO2016/057387
PCT Pub. Date: Apr. 14, 2016

(65) Prior Publication Data
US 2017/0298454 A1 Oct. 19, 2017

Related U.S. Application Data

(60) Provisional application No. 62/060,219, filed on Oct. 6, 2014.

(51) Int. Cl.
| | | |
|---|---|---|
| C12Q 1/68 | (2018.01) | |
| C12N 15/79 | (2006.01) | |
| G01N 33/53 | (2006.01) | |
| A61K 39/23 | (2006.01) | |
| C07H 21/04 | (2006.01) | |
| C12Q 1/6897 | (2018.01) | |
| C12Q 1/6886 | (2018.01) | |
| C12N 15/86 | (2006.01) | |

(52) U.S. Cl.
CPC ........ C12Q 1/6897 (2013.01); C12Q 1/6886 (2013.01); *C07H 21/04* (2013.01); *C12N 15/79* (2013.01); *C12N 15/86* (2013.01); *C12Q 2600/118* (2013.01); *C12Q 2600/156* (2013.01); *G01N 33/53* (2013.01)

(58) Field of Classification Search
CPC ...... C12N 15/79; C12N 15/86; C12Q 1/6886; C12Q 1/6897; C07H 21/04; G01N 33/53
USPC ............... 435/6, 7.1, 320.1, 6.1; 424/233.1; 536/23.7, 24.1
See application file for complete search history.

(56) References Cited

U.S. PATENT DOCUMENTS

| | | | |
|---|---|---|---|
| 6,083,716 A | 7/2000 | Wilson et al. | |
| 6,610,839 B1 | 8/2003 | Morin et al. | |
| 8,105,574 B2 | 1/2012 | Wilson et al. | |
| 9,846,157 B2 | 12/2017 | Hahn et al. | |
| 10,338,071 B2 | 7/2019 | Hahn et al. | |
| 2002/0037280 A1 | 3/2002 | Lieber et al. | |
| 2002/0102264 A1 | 8/2002 | Cheung | |
| 2003/0054555 A1 | 3/2003 | Farmer et al. | |
| 2003/0103963 A1 | 6/2003 | Cheung | |
| 2004/0203066 A1 | 10/2004 | Fisher et al. | |
| 2006/0115623 A1 | 6/2006 | Aizenberg et al. | |
| 2006/0160243 A1 | 7/2006 | Tang et al. | |
| 2007/0026381 A1 | 2/2007 | Huang et al. | |
| 2007/0026417 A1 | 2/2007 | Fuchs et al. | |
| 2007/0135013 A1 | 6/2007 | Faris | |
| 2007/0161051 A1 | 7/2007 | Tsinberg et al. | |
| 2007/0172903 A1 | 7/2007 | Toner et al. | |
| 2010/0310571 A1 | 12/2010 | Cheung | |
| 2011/0111480 A1 | 5/2011 | Fujiwara et al. | |
| 2011/0284110 A1 | 11/2011 | Gagnon | |
| 2012/0077246 A1 | 3/2012 | Hong et al. | |
| 2013/0121895 A1 | 5/2013 | Tang et al. | |

(Continued)

FOREIGN PATENT DOCUMENTS

| | | |
|---|---|---|
| WO | WO 1996/013597 | 5/1996 |
| WO | WO-2000/046355 A2 | 8/2000 |

(Continued)

OTHER PUBLICATIONS

Mizuguchi et al., Jul. 2014, US 20140199688 A1.*
Nichols et al., May 22, 2014, US 2014014151 A1.*
Maida et al., 2009, International Journal of Oncology, vol. 34, p. 1549-1556.*
Dorsey JF, et al. Tracking viable circulating tumor cells (CTCs) in the peripheral blood of non-small cell lung cancer (NSCLC) patients undergoing definitive radiation therapy: pilot study results. Cancer. Jan. 1, 2015;121(1):139-49. doi: 10.1002/cncr.28975. Epub Sep. 19, 2014.
Xu MJ, et al. A novel approach for the detection and genetic analysis of live melanoma circulating tumor cells. PLoS One. Mar. 25, 2015;10(3):e0123376. doi: 10.1371/journal.pone.0123376. eCollection 2015. (Published: Mar. 25, 2015).

(Continued)

*Primary Examiner* — Shin Lin Chen
(74) *Attorney, Agent, or Firm* — Howson & Howson LLP

(57) ABSTRACT

A method useful for identifying and isolating live circulating tumor cells is described. The method utilizes an adenoviral vector comprising a replication-competent adenovirus in which the E1 gene region is expressed under the control of a telomerase-specific promoter and further comprises a second expression cassette containing a marker protein, optionally fused to a detectable cell surface marker to permit detection of circulating tumor cells lacking cell surface markers. The method involves combining ex vivo a test sample from a patient suspected of having circulating tumor cells, an adenoviral probe system, and culture media for the cells. The test sample is incubated with the adenoviral system for a sufficient time to permit expression of the reporter protein. The marker gene expression can thereafter be quantitated and the marker-expressing cells may optionally be collected for further analysis.

23 Claims, 14 Drawing Sheets

(56) References Cited

U.S. PATENT DOCUMENTS

| | | |
|---|---|---|
| 2013/0288273 A1 | 10/2013 | Takagi et al. |
| 2014/0087362 A1 | 3/2014 | Szalay et al. |
| 2015/0285786 A1 | 10/2015 | Hahn et al. |
| 2018/0113130 A1 | 4/2018 | Hahn et al. |

FOREIGN PATENT DOCUMENTS

| | | |
|---|---|---|
| WO | WO 2003/046124 | 6/2003 |
| WO | WO 2005/001103 | 1/2005 |
| WO | WO 2009/073102 | 6/2009 |
| WO | WO 2009/073104 | 6/2009 |
| WO | WO 2009/105084 | 8/2009 |
| WO | WO 2012/071318 | 5/2012 |
| WO | WO 2013/173702 | 11/2013 |
| WO | WO 2014/065861 A1 | 5/2014 |

OTHER PUBLICATIONS

Xu MJ, et al. Circulating Tumor Cells, DNA, and mRNA: Potential for Clinical Utility in Patients With Melanoma. Oncologist. Jan. 2016;21(1):84-94. doi: 10.1634/theoncologist.2015-0207. Epub Nov. 27, 2015.

Wang, et al. "Construction and expression of human EpCAM eukaryotic expression vectors and identification of their products." Xi bao yu fen zi mian yi xue za zhi= Chinese journal of cellular and molecular immunology 20.6 (2004): 765-768. (Nov. 2004).

Wang, et al. Webpage < https://www.ncbi.nlm.nih.gov/pubmed/15555457>, 1 page, retrieved from Internet on Jul. 20, 2018. Abstract of "Construction and expression of human EpCAM eukaryotic expression vectors and identification of their products." Xi bao yu fen zi mian yi xue za zhi= Chinese journal of cellular and molecular immunology 20.6 (2004): 765-768. (Nov. 2004).

Wang, et al. HPtaa database-potential target genes for clinical diagnosis and immunotherapy of human carcinoma. Nucleic Acids Res. Jan. 1, 2006;34(Database issue):D607-12 (Published: Jan. 1, 2006).

Van Der Bruggen, et al. Peptide database: T cell-defined tumor antigens. Cancer Immun 2013. Web page <http://www.cancerimmunity.org/peptide/>, 4 pages, Last updated: Apr. 10, 2013, retrieved from Internet Archive Wayback Machine < https://web.archive.org/web/20140915111116/http://www.cancerimmunity.org/peptide/> on Jul. 20, 2018.

Restriction Requirement dated May 11, 2018 issued in U.S. Appl. No. 15/812,105.

Applicant's Response filed Jul. 11, 2018 to Restriction Requirement dated May 11, 2018 issued in U.S. Appl. No. 15/812,105.

Restriction Requirement dated Jan. 25, 2016 issued in U.S. Appl. No. 14/438,321.

Applicant's Response filed Mar. 23, 2016 to Restriction Requirement dated Jan. 25, 2016 issued in U.S. Appl. No. 14/438,321.

Boshart, et al. "A very strong enhancer is located upstream of an immediate early gene of human cytomegalovirus." cell 41.2 (1985): 521-530.(Jun. 1985).

Chapman, et al. "Improved survival with vemurafenib in melanoma with BRAF V600E mutation." New England Journal of Medicine 364.26 (2011): 2507-2516. (Jun. 2011).

Chiu, et al. "Genome-wide characterization of circulating tumor cells identifies novel prognostic genomic alterations in systemic melanoma metastasis." Clinical chemistry 60.6 (2014): 873-885. (Epub Apr. 2014).

Cristofanilli, et al. "Circulating tumor cells, disease progression, and survival in metastatic breast cancer." N Engl J Med 2004.351 (2004): 781-791. (Aug. 2004).

Dorsey, et al. "Tracking viable circulating tumor cells (CTCs) in the peripheral blood of non-small cell lung cancer (NSCLC) patients undergoing definitive radiation therapy: Pilot study results." Cancer 121.1 (2015): 139-149. (Sep. 2014).

Fero et al. "Automated quantitative live cell fluorescence microscopy." Cold Spring Harbor perspectives in biology 2.8 (2010): a000455. (Jun. 30, 2010).

Fisher, et al. "Biochemical and functional analysis of an adenovirus-based ligand complex for gene transfer." Biochemical Journal 299.1 (1994): 49-58. (Apr. 1, 1994).

Glasspool, et al. "The hTERT and hTERC telomerase gene promoters are activated by the second exon of the adenoviral protein, E1 A, identifying the transcriptional corepressor CtBP as a potential rearessor of both genes." Neoplasia 7.6 (2005): 614-622. (Jun. 2005).

Hoshimoto, et al. "Assessment of prognostic circulating tumor cells in a phase III trial of adjuvant immunotherapy after complete resection of stage IV melanoma." Annals of surgery 255.2 (2012): 357. (Feb. 2012).

Hoshimoto, et al. "Association between circulating tumor cells and prognosis in patients with stage III melanoma with sentinel lymph node metastasis in a phase III international multicenter trial." Journal of clinical oncology 30.31 (2012): 3819-3826. (Sep. 2012).

Jarkowski, et al. "Controversies in the Management of Advanced Melanoma: "Gray" Areas Amid the "Black and Blue"." Annals of Pharmacotherapy 48.11 (2014): 1456-1468. (Epub Jul. 23, 2014).

Ju, et al. "Application of a telomerase-based circulating tumor cell (CTC) assay in bladder cancer patients receiving postoperative radiation therapy: a case study." Cancer biology & therapy 15.6 (2014): 683-687.(Epub Mar. 11, 2014).

Kang, et al. "Shifted termination assay (STA) fragment analysis to detect BRAF V600 mutations in papillary thyroid carcinomas." Diagnostic pathology 8.1 (2013): 121. (Published online Jul. 24, 2013).

Karakousis, et al. "Circulating melanoma cells as a predictive biomarker." Journal of Investigative Dermatology 133.6 (2013): 1460-1462. (Jun. 2013).

Khoja, et al. "Biomarker utility of circulating tumor cells in metastatic cutaneous melanoma." Journal of Investigative Dermatology 133.6 (2013): 1582-1590. (Epub Dec. 6, 2012).

Kim et al. "Specific association of human telomerase activity with immortal cells and cancer." Science (1994): 2011-2015. (Dec. 1994).

Kudo, et al. "Novel cell and tissue acquisition system (CTAS): Microdissection of live and frozen brain tissues." PloS one 7.7 (2012): e41564. (Epub Jul. 24, 2012).

Lim, et al. "Coexistence of two distinct G-quadruplex conformations in the hTERT promoter." Journal of the American Chemical Society 132.35 (2010): 12331-12342.

Lin, et al. "Polyclonality of BRAF mutations in primary melanoma and the selection of mutant alleles during progression." British journal of cancer 104.3 (2011): 464-468. (Epub Jan. 11, 2011).

Long, et al. "Prognostic and clinicopathologic associations of oncogenic BRAF in metastatic melanoma." Journal of Clinical Oncology 29.10 (2011): 1239-1246. (Epub Feb. 22, 2011).

Luo, et al. "Isolation and molecular characterization of circulating melanoma cells." Cell reports 7.3 (2014): 645-653. (Epub Apr. 18, 2014).

Macarthur, et al. "Detection of brain tumor cells in the peripheral blood by a telomerase promoter-based assay." Cancer research 74.8 (2014): 2152-2159. (Epub Feb. 13, 2014).

Mocellin, et al. "The prognostic value of circulating tumor cells in patients with melanoma: a systematic review and meta-analysis." Clinical cancer research 12.15 (2006): 4605-4613. (Aug. 2006).

Nicholl, et al. "Molecular upstaging based on paraffin-embedded sentinel lymph nodes: ten-year follow-up confirms prognostic utility in melanoma patients." Annals of surgery 253.1 (2011): 116. (Jan. 2011).

Okwan-Duodu, et al. "Role of radiation therapy as immune activator in the era of modern immunotherapy for metastatic malignant melanoma." American journal of clinical oncology 38.1 (2015): 119-125. (Feb. 2015).

Pantel, et al. "Detection, clinical relevance and specific biological properties of disseminating tumour cells." Nature Reviews Cancer 8.5 (2008): 329-340. (Apr. 2008).

(56) References Cited

OTHER PUBLICATIONS

Paterlini-Brechot, et al. "Circulating tumor cells (CTC) detection: clinical impact and future directions." Cancer letters 253.2 (2007): 180-204. (Epub Feb. 20, 2007).
Postow, et al. "Immunologic correlates of the abscopal effect in a patient with melanoma." New England Journal of Medicine 366.10 (2012): 925-931. (Mar. 2012).
Rao, et al. "Circulating melanoma cells and survival in metastatic melanoma." International journal of oncology 38.3 (2011): 755-760. (Epub Jan. 3, 2011).
Sakaizawa, et al. "Mutation analysis of BRAF and KIT in circulating melanoma cells at the single cell level." British journal of cancer 106.5 (2012): 939-946. (Epub Jan. 26, 2012).
Scoggins, et al. "Prospective multi-institutional study of reverse transcriptase polymerase chain reaction for molecular staging of melanoma." Journal of clinical oncology 24.18 (2006): 2849-2857. (Jun. 2006).
Shay, J. W., et al. "A survey of telomerase activity in human cancer." European journal of cancer 33.5 (1997): 787-791. (Apr. 1997).
Slanchev, et al. "The epithelial cell adhesion molecule EpCAM is required for epithelial morphogenesis and integrity during zebrafish epiboly and skin development." PLoS genetics 5.7 (2009): e1000563. (Epub Jul. 17, 2009).
Stamell, et al. "The abscopal effect associated with a systemic anti-melanoma immune response." International Journal of Radiation Oncology Biology Physics 85.2 (2013): 293-295. (Epub May 5, 2012).
Steen, et al. "Circulating tumor cells in melanoma: a review of the literature and description of a novel technique." Proceedings (Baylor University. Medical Center) 21.2 (2008): 127. (Apr. 2008).
Su, et al. "Targeting gene expression selectively in cancer cells by using the progression-elevated gene-3 promoter." Proceedings of the National Academy of Sciences of the United States of America 102.4 (2005): 1059-1064. (Jan. 2005).
Vigneron, et al. "Database of T cell-defined human tumor antigens: the 2013 update." Cancer Immunity Archive 13.3 (2013): 15. (Jan. 2013).
Wu et al. "Targeting genes: delivery and persistent expression of a foreign gene driven by mammalian regulatory elements in vivo." Journal of Biological Chemistry 264.29 (1989): 16985-16987. (Oct. 1989).
Yaron, et al. "A convenient, optimized pipeline for isolation, fluorescence microscopy and molecular analysis of live single cells." Biological procedures online 16.1 (2014): 9. (May 8, 2014).
Yu, et al. "Circulating tumor cells: approaches to isolation and characterization." The Journal of cell biology 192.3 (2011): 373-382. (Feb. 2011).
Zong, et al. "Genome-wide detection of single-nucleotide and copy-number variations of a single human cell." Science 338.6114 (2012): 1622-1626. (Dec. 2012).
Fallaux, et al. "New helper cells and matched early region 1-deleted adenovirus vectors prevent generation of replication-competent adenoviruses." Human gene therapy 9.13 (1998): 1909-1917. (Sep. 1998).
International Search Report and Written Opinion for parent International Patent Application No. PCT/US2015/053982 dated Dec. 29, 2015.
Alunni-Fabbroni et al., "Circulating tumour cells in clinical practice: Methods of detection and possible characterization", Methods, vol. 50(2010):289-297, Jan. 2010.
Bhang et al., Tumor-specific imaging through progression elevated gene-3 promoter-driven gene expression, Nature Medicine, vol. 17(1):123-129, Dec. 12, 2010.
Chen et al., "Nanoroughened Surfaces for Efficient Captre of Circulating Tumor Cells without Using Capture Antibodies", ACS Nano, vol. 7(1):566-575, Oct. 2012.
Hearing et al., Identification of a Repeated Sequence Element Required for Efficient Encapsidation of the Adenovirus Type 5 Chromosome, Journal of Virology, vol. 61(8):2555-2558, Aug. 1, 1987.
NIH Report, "Project Information 1R03CA165182-01 (Abstract)", Sep. 2012.
Steinwaerder et al., DNA Replication of First-Generation Adenovirus Vectors in Tumor Cells, Human Gene Therapy, vol. 11:1933-1948, Sep. 1, 2000.
Steinwaerder et al., Tumor-specific gene expression in hepatic metastases by a replication-activated adenovirus vector, Nature Medicine, vol. 7(2):240-243, Feb. 1, 2001.
Thierry et al., "Herceptin functionalized microfluidic polydimethylsiloxane devices for the capture of human epidermal growth factor receptor 2 positive circulating breast cancer cells", Biomicrofluidics, vol. 4:032205-1-032205-10, Apr. 2010.
Wan et al., "Lab on a Chip: Electronic Supplementary Information, Capture, Isolation and Release of Cancer Cells with Aptamer-functionalized Glass bead Array", The Royal Society of Chemistry, Jan. 2012.
International Search Report and Written Opinion issued for International Patent Application No. PCT/US2013/031698, dated May 7, 2013.
Office Action dated Aug. 26, 2016 issued in U.S. Appl. No. 14/438,321.
Applicant's Response filed Nov. 28, 2016 to the Office Action dated Aug. 26, 2016 issued in U.S. Appl. No. 14/438,321.
Office Action dated Mar. 23, 2017 issued in U.S. Appl. No. 14/438,321.
Applicant's Response filed Jun. 23, 2017 to the Office Action dated Mar. 23, 2017 issued in U.S. Appl. No. 14/438,321.
Chinniah et al., Early Detection of Recurrence in Patients with Locally Advanced Non-small Cell Lung Cancer via Circulating Tumor Cell Analysis. Clinical Lung Cancer, In press. Available online May 4, 2019.
Frick et al., Circulating Tumor Cell Assessment in Presumed Early Stage Non-Small Cell Lung Cancer Patients Treated with Stereotactic Body Radiation Therapy: A Prospective Pilot Study. Int J Radiat Oncol Biol Phys. Nov. 1, 2018;102(3):536-542. doi: 10.1016/j.ijrobp.2018.06.041. Epub Jul. 2, 2018.
Office Action dated Nov. 14, 2018 issued in U.S. Appl. No. 15/812,105.
Applicant's Response filed Feb. 8, 2019 to the Nov. 14, 2018 Office Action issued in U.S. Appl. No. 15/812,105.
Kojima et al., A simple biological imaging system for detecting viable human circulating tumor cells, The Journal of Clinical Investigation, vol. 119(10):3172-81, Oct. 2009.

\* cited by examiner

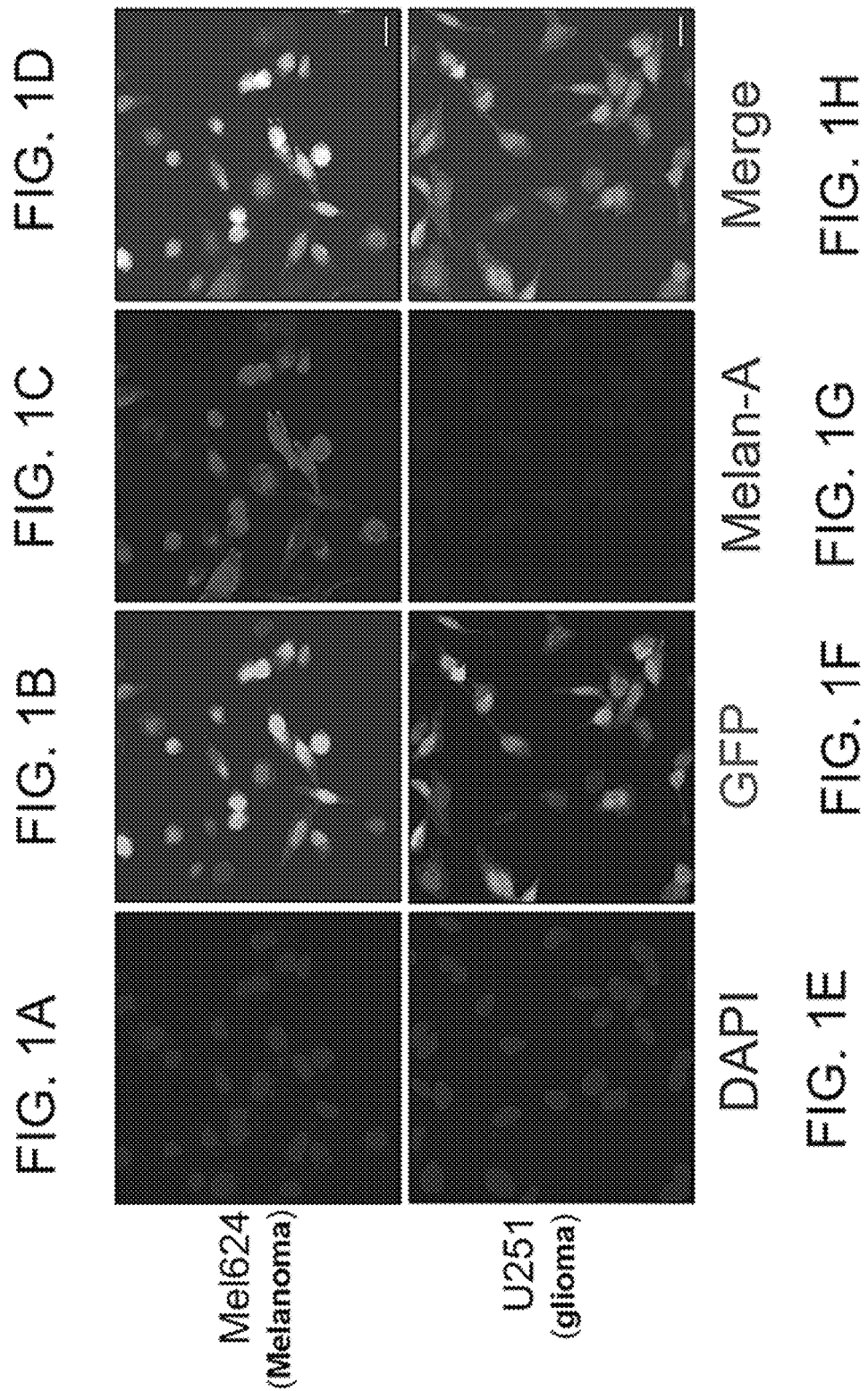

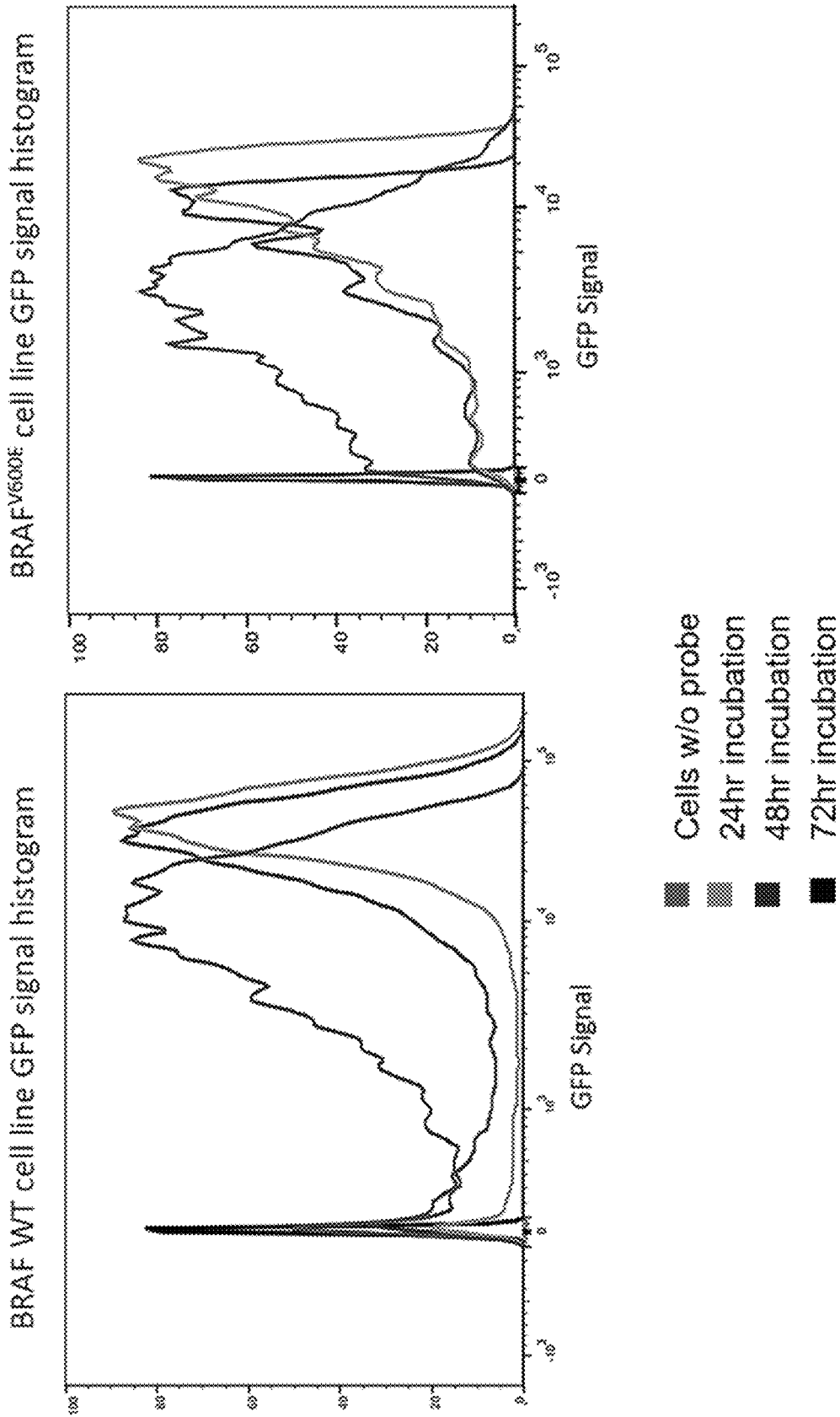

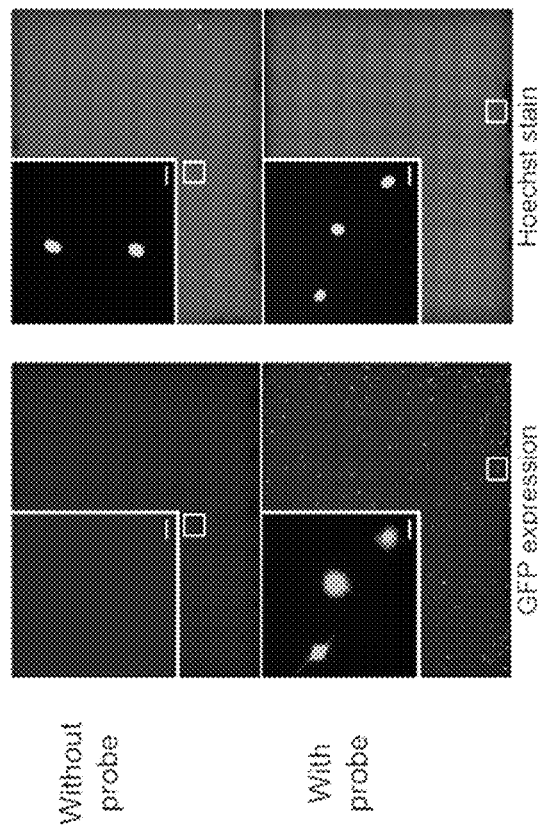
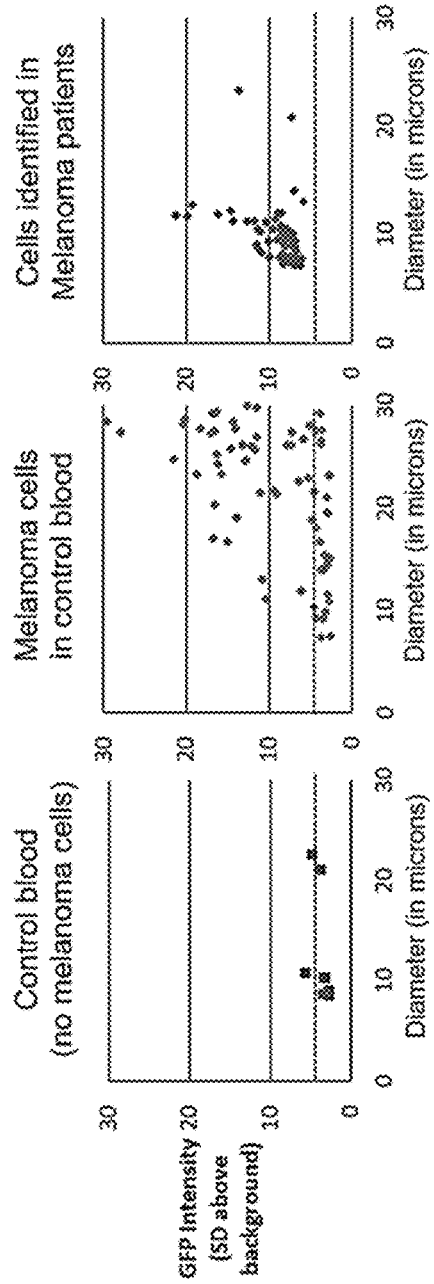

FIG. 4A
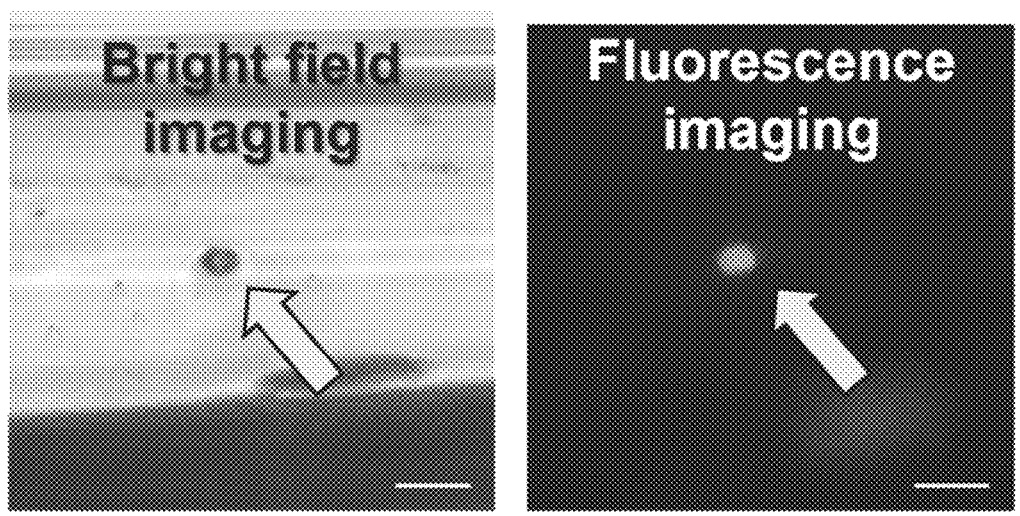
WGA & qPCR
→
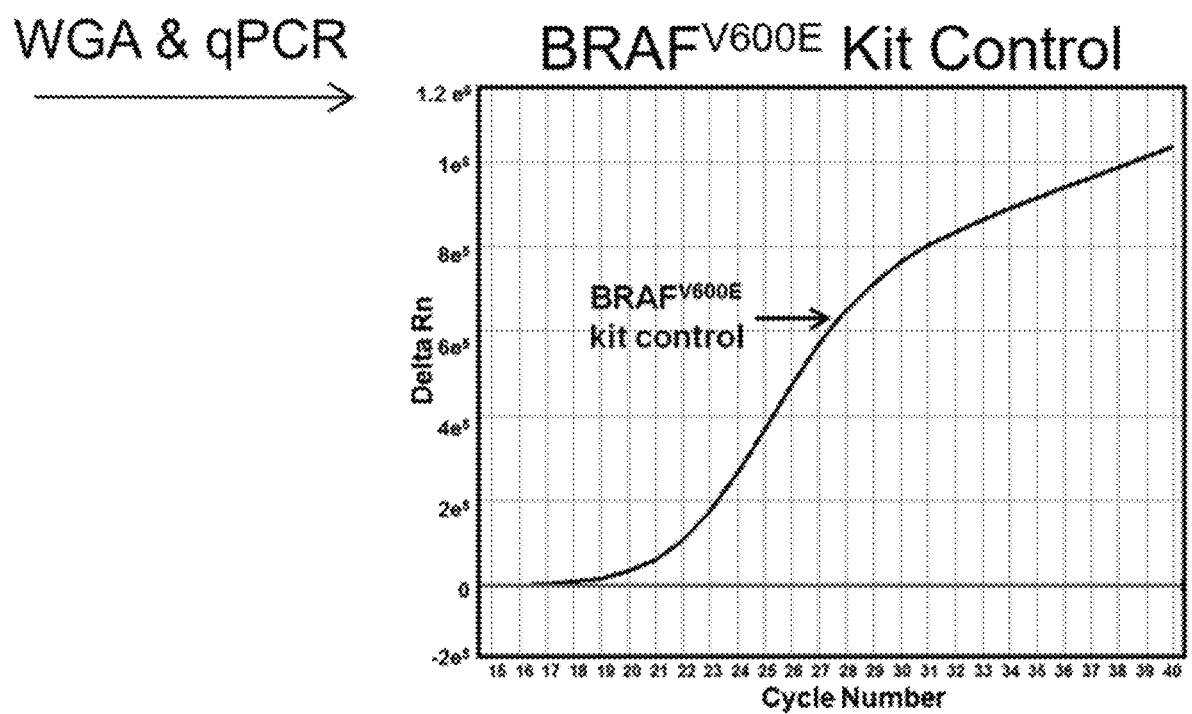

FIG. 4B
A375P in culture
BRAF$^{V600E/V600E}$
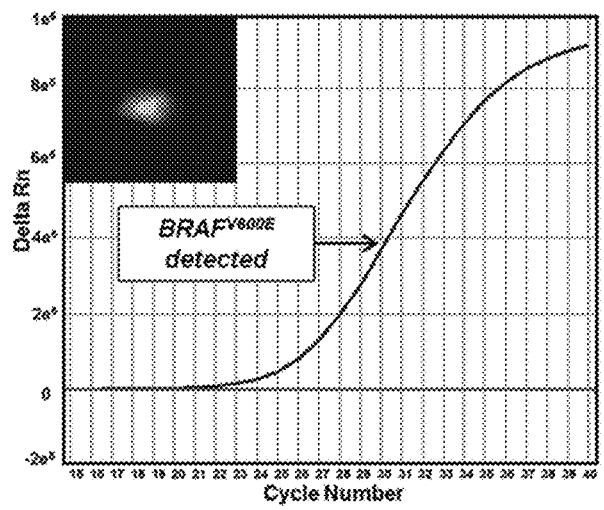
Mel624 in culture
BRAF$^{WT/V600E}$
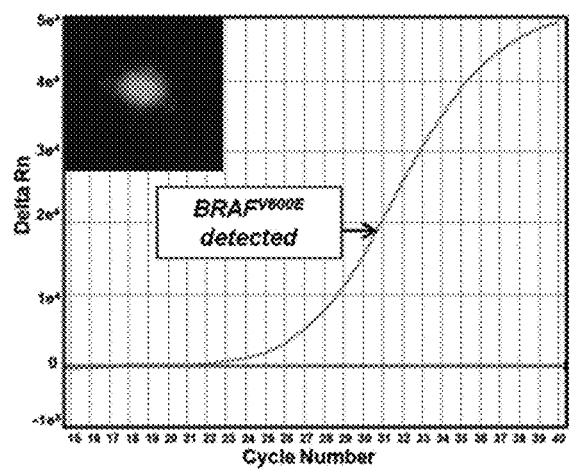
MeWo in culture
BRAF$^{WT/WT}$
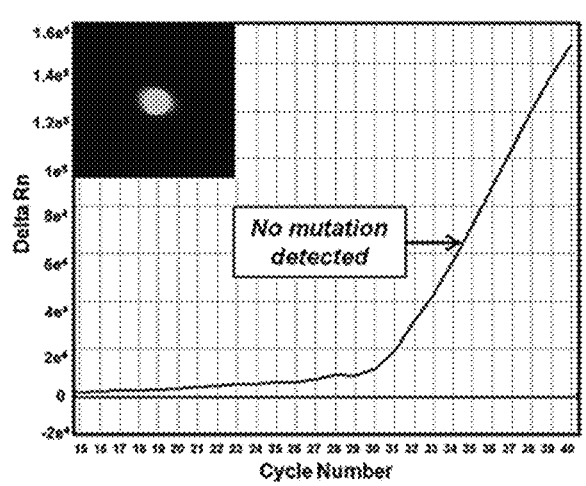

FIG. 4C
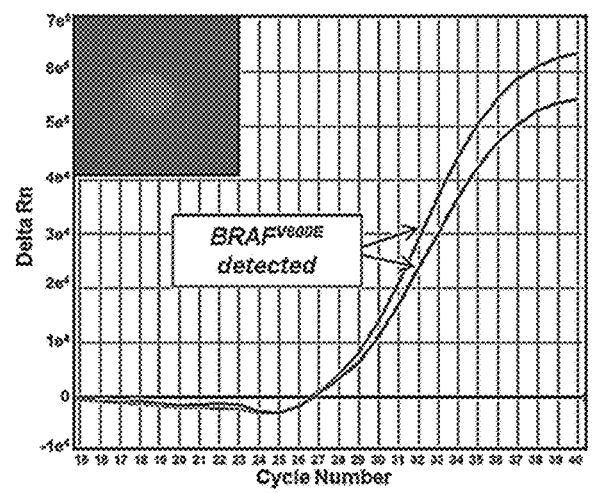
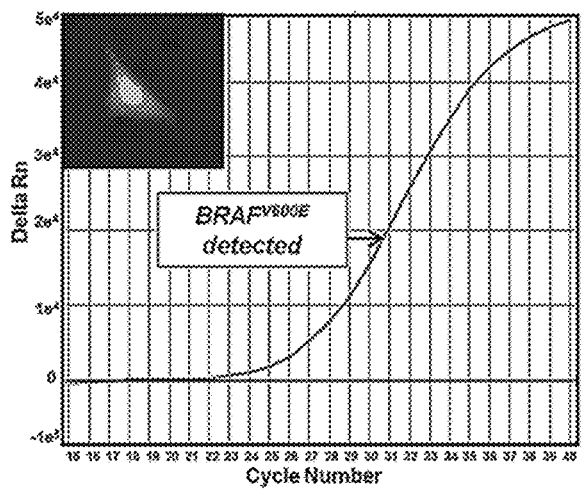
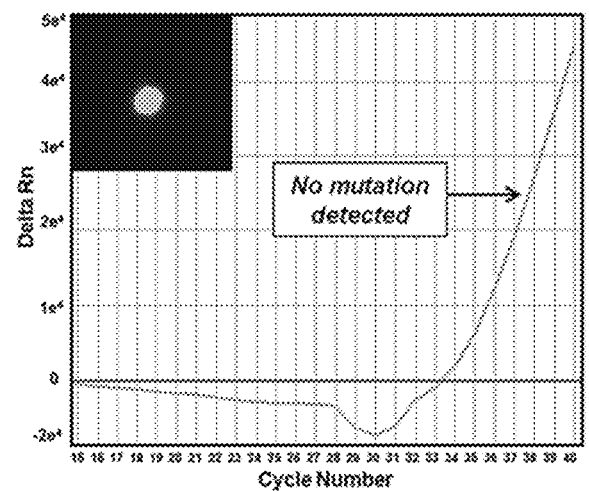

FIG. 4D
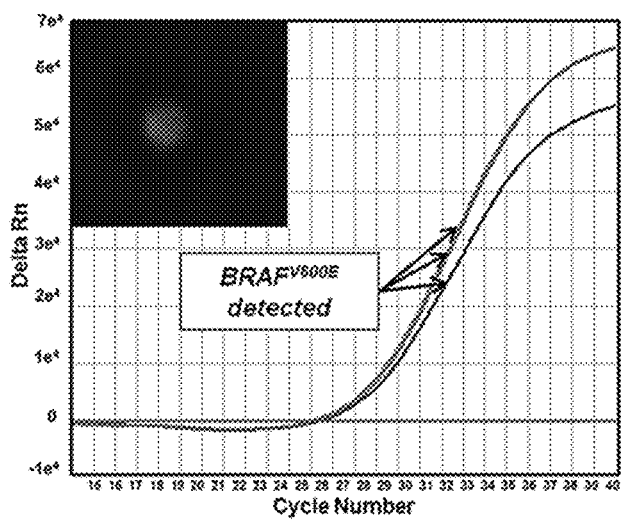
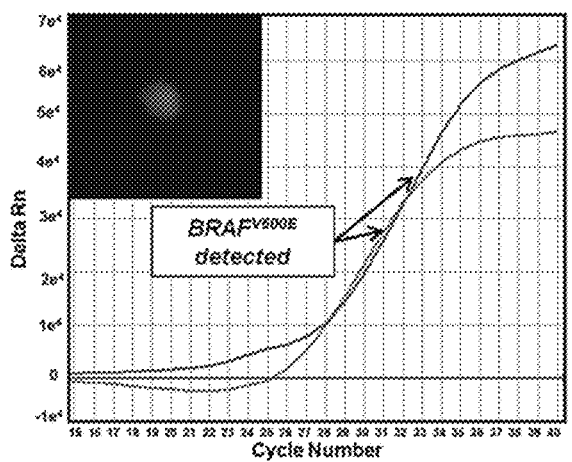
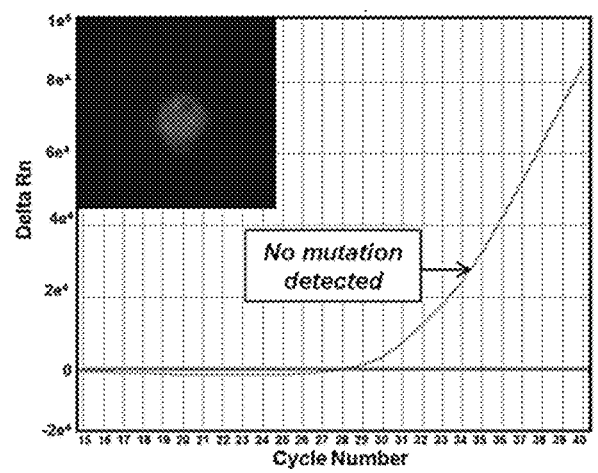
| Patient | Primary tumor BRAF mutation status | CTC sample BRAF mutation status |
|---|---|---|
| W | V600E | V600E |
| X | V600E | V600E |
| Y | V600E | V600E |
| Z | WT | WT |

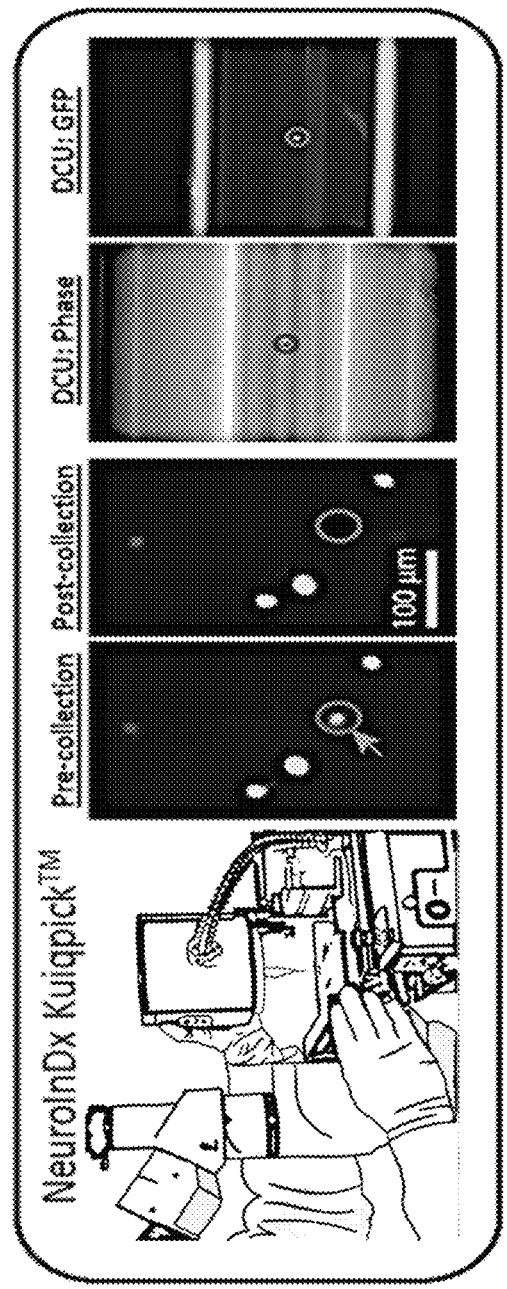

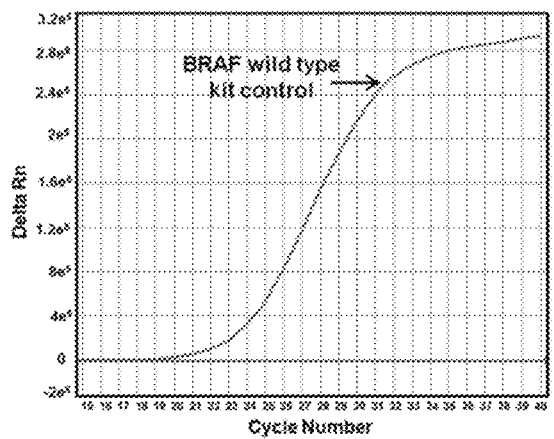
FIG. 7A
BRAF WT Kit Control
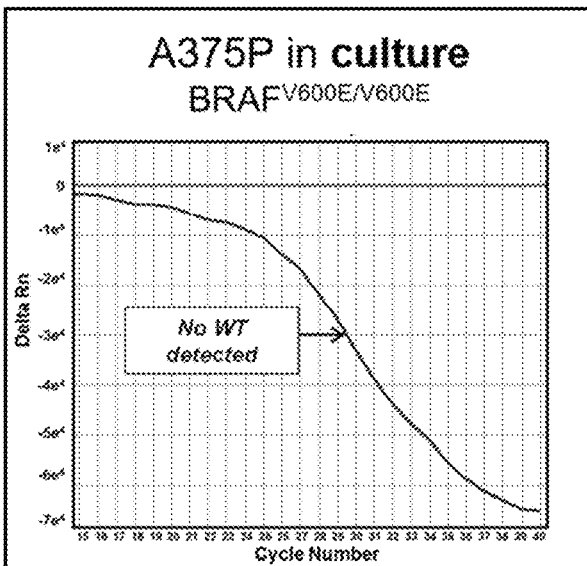
FIG. 7B
A375P in culture
BRAF$^{V600E/V600E}$
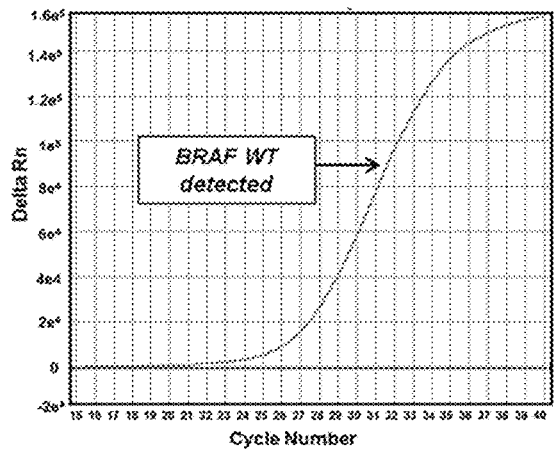
Mel624 in culture
BRAF$^{WT/V600E}$
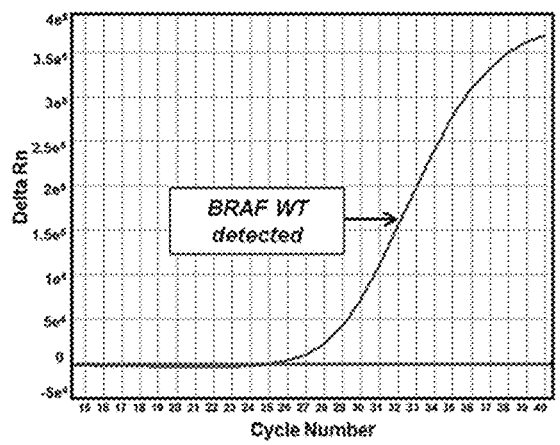
MeWo in culture
BRAF$^{WT/WT}$ FIG. 7C
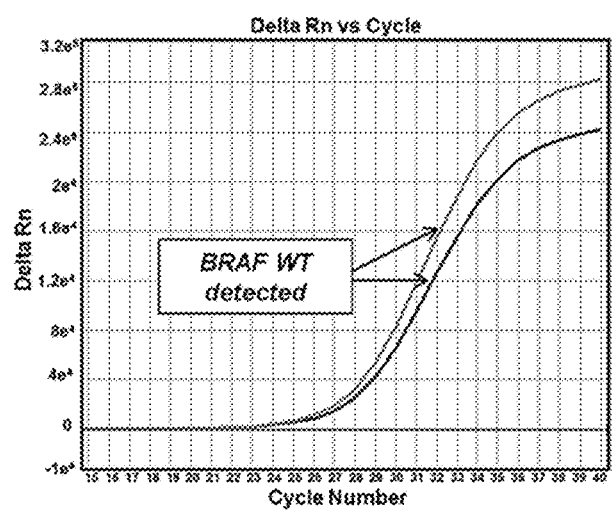
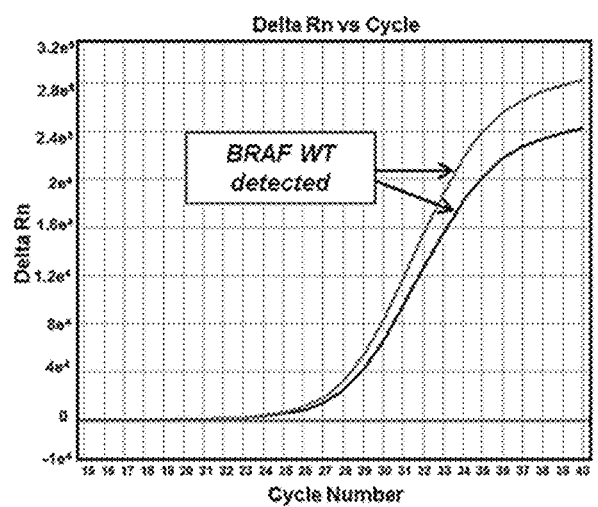
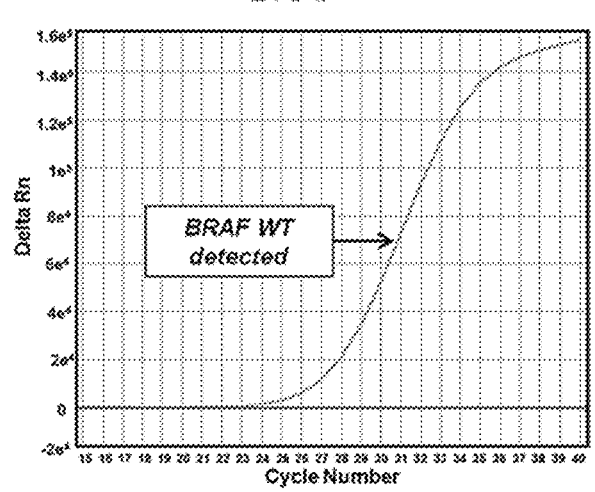

FIG. 7D
Patient W
Primary tumor: BRAF$^{V600E}$
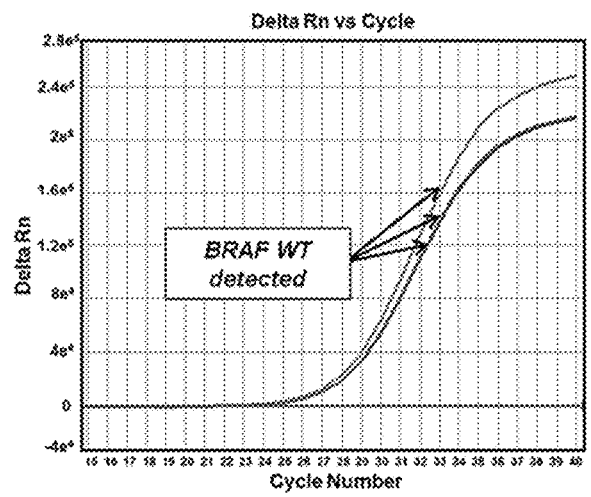
Patient Y
Primary tumor: BRAF$^{V600E}$
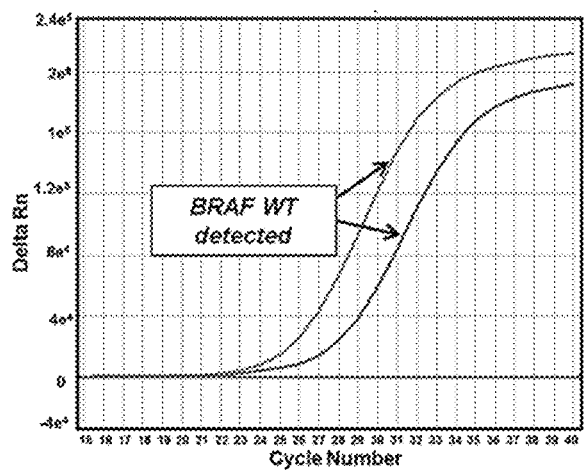
Patient Z
Primary tumor: BRAF WT
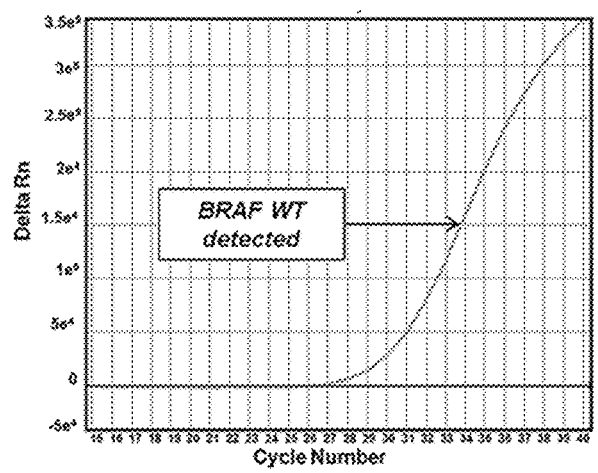

COMPOSITIONS AND METHODS FOR ISOLATION OF CIRCULATING TUMOR CELLS (CTC)

CROSS-REFERENCE TO RELATED APPLICATIONS

This is a 371 national stage of PCT/US2015/053982, filed Oct. 5, 2015, which claims the benefit under 35 USC 119(e) of U.S. Provisional Patent Application No. 62/060,219, filed Oct. 6, 2014.

STATEMENT OF FEDERALLY SUPPORTED RESEARCH

This invention was made with government support under grant numbers CA145075 and NS076548 awarded by the National Institutes of Health. The government has certain rights in the invention.

BACKGROUND OF THE INVENTION

Melanoma is the fifth most common solid malignancy in the United States, affecting 76,000 individuals each year [U.S. Cancer Statistics Working Group. United states cancer statistics: 1999-2008 Incidence and mortality web-based report 2012]. Stage I disease has a 5-year survival rate of 92%, but survival drops precipitously for Stage II, III, and IV disease to 53%, 40%, and 15%, respectively [American Cancer Society. What are the survival rates for melanoma skin cancer by stage? http://www.cancer.org/cancer/skincancer-melanoma/detailedguide/melanoma-skin-cancer-survival-rates. Updated 2013. Accessed 16/July, 2013]. New treatments have been recently developed, including targeted therapies and immune modulators in patients with advanced disease. Addition interest in combining immunomodulation and radiation therapy in patients with advanced melanoma have been fueled by the observation of abscopal effects, in which regression of metastatic cancer occurs distant from the irradiated site. [Postow M A, et al. N Engl J Med. 2012; 366(10):925-931; Stamell E F, International Journal of Radiation Oncology* Biology* Physics. 2013; 85(2):293-295; Okwan-Duodu D, Am. J. Clin. Oncol. http://dx.doi.org/10.1097/COC.0b013e3182940dc3. 2013]. However, how best to monitor or stratify patients for different treatments or to detect early treatment failure remains unclear [Jarkowski A, 3rd, Norris L, Trinh V A. Controversies in the management of advanced melanoma: "Gray" areas amid the "black and blue". Ann Pharmacother. 2014].

Circulating tumor cell (CTC) analysis may assist in the clinical management of melanoma. CTCs are cancer cells that have dissociated from the primary tumor and can be identified in peripheral blood through blood draws obtained with minimal risk [Paterlini-Brechot P, Benali N L. Circulating tumor cells (CTC) detection: Clinical impact and future directions. Cancer Lett. 2007; 253(2):180-204]. CTCs are rare, usually representing no more than one in one million peripheral blood cells, and potentially carry prognostic significance, as suggested in studies of breast, colorectal, and prostate cancers. Paterline-Berchot, supra; Steen S, Circulating tumor cells in melanoma: A review of the literature and description of a novel technique. Proc (Bayl Univ Med Cent). 2008; 21(2):127-132; Cristofanilli M, et al. Circulating tumor cells, disease progression, and survival in metastatic breast cancer. N Engl J Med. 2004; 351(8):781-791; Pantel K, Brakenhoff R H, Brandt B. Detection, clinical relevance and specific biological properties of disseminating tumour cells. Nat Rev Cancer. 2008; 8(5):329-340]. Serial CTC counts before and after treatment may also help clarify disease status or risk of recurrence.

Because melanoma is derived from neural crest cells and thus often exhibits mesenchymal features, conventional CTC detection platforms designed for epithelial cancers using cell surface markers (such as epithelial cell adhesion molecule, EpCAM) may not be optimal for patients with melanoma. However, alternative cell surface markers, such as melanoma-specific cell surface proteoglycans, have aided the detection of CTCs in melanoma patients [Rao C, et al. Int J Oncol. 2011; 38(3):755-760; Khoja L, et al., J Invest Dermatol. 2013; 133(6):1582-1590; Karakousis G, et al., J Invest Dermatol. 2013; 133(6):1460-1462; Sakaizawa K, et al., Br J Cancer. 2012; 106(5):939-946; Luo X, et al. Isolation and molecular characterization of circulating melanoma cells. Cell reports. 2014; 7(3):645-653]. Clinical studies utilizing reverse transcriptase polymerase chain reaction (RT-PCR) to identify melanoma-specific RNA products in the blood have suggested potential prognostic value [Mocellin S, et al, Clin Cancer Res. 2006; 12(15):4605-4613; Nicholl M B, et al., Ann Surg. 2011; 253(1):116-122; Hoshimoto S, et al. Ann Surg. 2012; 255(2):357-362; Hoshimoto S, et al. J Clin Oncol. 2012; 30(31):3819-3826; Scoggins C R, et al, J Clin Oncol. 2006; 24(18):2849-2857]. Variability of cell surface marker expression or the uncertainty of the precise cellular origin of RT-PCR products, such as whether they are derived from live, dead, or dying cells, present biological or technical hurdles with these CTC detection methods.

Telomerase is an enzyme that protects the ends of chromosomes to forestall senescence, and is upregulated in almost all tumor cells to help confer immortality [Shay J W, Eur J Cancer. 1997; 33(5):787-791; Kim N W, et al, Science. 1994; 266(5193):2011-2015]. In contrast, telomerase is downregulated in almost all normal cells, which are thus susceptible to senescence.

Onclys BioPharma and Sysmex have described a commercial venture utilizing recombinant adenoviruses expressing green fluorescent protein for in vitro use in detecting circulating liver cells in blood. Additionally, systems for detecting CTC using non-lytic adenoviruses have been described. See, e.g., WO 2014/065861. However, this system does not permit distinguishing between live and dead tumor cells.

What are needed are more accurate systems for detecting circulating tumor cells.

SUMMARY OF THE INVENTION

The present invention provides compositions and methods for identifying, enumerating, and isolation of live circulating tumor cells. This assay permits monitoring of the status of disease for patients and provides genetic information about the tumor cells.

In one aspect, the invention provides a method useful for isolating live circulating tumor cells. The method comprises combining ex vivo a test sample from a patient suspected of having circulating tumor cells, an adenoviral probe system, and culture media for the cells. The adenoviral probe system comprises: (i) a first replication competent adenoviral particle having an adenoviral capsid in which at least a first expression cassette is packaged, said expression cassette comprising an adenoviral 5' ITR, an tumor-specific promoter which is specifically activated in the presence of circulating tumor cells, and an adenoviral 3' ITR; and (ii) a coding sequence for a first reporter protein which is expressed in the presence of circulating tumor cells, and an adenoviral 3' ITR. The method further comprises incubating the test sample and adenoviral system for a sufficient time to permit expression of the reporter protein, optionally replenishing the media; and collecting cells expressing the first reporter protein, whereby expression of the first reporter protein indicates the presence of live circulating tumor cells in the sample. In one embodiment, the tumor-specific promoter is a human telomerase reverse transcriptase (hTERT) promoter. In another embodiment, the first expression cassette comprises an adenoviral E1a coding region and E1b coding region under the control of the tumor specific promoter. In a further embodiment, the first adenoviral particle further comprises a second expression cassette comprising a second fluorescent protein gene sequence under the control of regulatory sequences which direct expression thereof in the cell.

In a further aspect, the invention provides a method useful for isolating circulating tumor cells. The method comprises combining ex vivo a test sample from a patient suspected of having circulating tumor cells, an adenoviral probe system, and culture media for the cells. The adenoviral probe system comprises (i) a first replication competent adenoviral particle having an adenoviral capsid in which at least a first expression cassette is packaged, said expression cassette comprising an adenoviral 5' ITR, an tumor-specific promoter which is specifically activated in the presence of circulating tumor cells, and an adenoviral 3' ITR; and (ii) a coding sequence for a first reporter protein which is preferentially expressed in the presence of live circulating tumor cells, and an adenoviral 3' ITR. The method further comprises incubating the test sample and adenoviral system for a sufficient time to permit expression of the reporter protein, and optionally replenishing the media. Further, the method comprises one or more of: collecting fluorescent cells; extracting total genomic DNA; amplifying total DNA; purifying amplified DNA; and analyzing the purified DNA for a selected tumor associated mutation or a drug associated mutation in a tumor.

In a further aspect, the invention provides a product comprising a novel vector system for use in a telomerase based assay for detecting circulating tumor cells in vitro. The system comprises (a) a first replication competent adenoviral particle having an adenoviral capsid in which at least a first expression cassette is packaged, said expression cassette comprising an adenoviral 5' ITR, an tumor-specific promoter which is specifically activated in the presence of circulating tumor cells, and an adenoviral 3' ITR; and (b) a coding sequence for a first reporter protein which is expressed in the presence of circulating tumor cells, and an adenoviral 3' ITR. In one embodiment, the first expression cassette comprises an adenoviral E1a coding region and E1b coding region which expresses E1a and E1b products sufficient for replication of the first adenoviral particle, said coding regions being the control of the tumor specific promoter.

In another aspect, the product contains one or more carriers for the vectors. Optionally, the product may contain one or more of container with a diluent, a slide or plate with wells, cell media, a ligand for a fluorescent protein, a magnetic bead comprising an antibody for the fluorescent protein, and a syringe.

Still other aspects and advantages of the invention will be apparent from the detailed description of the invention.

BRIEF DESCRIPTION OF THE DRAWINGS

FIGS. 1A-FIG. 1J relates to the pre-clinical characterization of melanoma cells. In FIGS. 1A-1H, melanoma and glioma cells (Me1624 and U251 are shown respectively in the top and bottom rows, as representative examples) were incubated with the probe, followed by immunofluorescence staining for Melan-A. Robust GFP expression indicate probe efficacy in melanoma comparable to glioma. The identity of melanoma cells and lack of effect on protein expression due to exposure to probe is confirmed by the coincidence of the GFP and Melan-A expression. Each row shows the same cells, with DAPI as a nuclear stain in the left-most panel, and the rightmost panel (Merge) show merging of all three fluorescent channels. Bar, 30 um. FIGS. 1I-1J provides the results of flow cytometry analysis of BRAF WT (MeWo) and BRAF mutated (Me1624) cells indicated that for both cell lines, GFP signal peaked after 48 hours of exposure to the probe, with no further increase after 72 hours.

FIGS. 2A-2F illustrate the integration of an illustrative replication-competent adenoviral probe with a semi-automated, computer-driven image acquisition and analysis system. FIGS. 2A-2D illustrate melanoma cells (A375P cells shown here as a representative example) incubated with the probe for 24 hours were visualized under fluorescent microscopy. Tiled images were taken for each well. Hoechst dye was added before image acquisition to delineate nucleated cells, which take up the dye and emit blue fluorescent signal under UV light. Bar, 30 um. FIG. 2E provides scatter plots showing individual cells, plotting size (X-axis) and fluorescent intensity (standard deviations (SD) above background) (Y-axis) identified by the imaging program. Control blood studies with spiked melanoma cells (middle graph) or without (left graph) demonstrated that a stringent GFP intensity cutoff (black dotted line) excluded false positive signals and contributed to greater specificity for patient samples. The size and fluorescent intensify cutoffs were applied to the blood samples of patients with metastatic melanoma (data from a representative patient is shown in the right graph).

FIG. 2F provides confirmation of melanoma origin of CTCs. Patient samples were fixed and immunofluorescence staining for Melan-A and DAPI was performed. The DAPI+/GFP+/Melan-A+ (arrows) cells were identified as melanoma CTCs while the surrounding DAPI+ only cells (arrowheads) were found to be white blood cells. Bar, 30 μM.

FIGS. 4A-4D illustrates detection of DNA mutations in isolated CTCs. FIG. 4A Isolation, processing, and analysis of individual cells. Cells exposed to the probe and rendered fluorescent were individually isolated via capillary-based methods. The individual cells within the glass capillary tubes can be visualized under bright field (left) and fluorescence microscopy (right). Whole genome amplification (WGA) was performed on the DNA extracted from each cell, followed by quantitative polymerase chain reaction (qPCR) analysis using primers specific for the $BRAF^{V600E}$ mutation. The presence of the mutation results in signal (Delta Rn, Y-axis) detectable by the $28^{th}$ cycle and a curve of the characteristic shape (as shown in the graph resulting from the $BRAF^{V600E}$ kit control). Bar, 30 um. (B) Isolation and genetic analysis of melanoma cells in culture. A375P (homozygous $BRAF^{V600E}$ mutated), Me1624 (heterozygous $BRAF^{V600E}$ mutated), and MeWo (homozygous BRAF WT) cells were isolated using the capillary-based technique described. The DNA was extracted from each cell and subject to WGA, followed by qPCR analysis with primers specific for the $BRAF^{V600E}$ mutation. Inset images show representative isolated cells. In each case, the qPCR analysis confirms the specific BRAF status of the parental cells in culture. (C) Isolation and genetic analysis of melanoma cells spiked into control blood. Melanoma cells were prepared as in (B) but spiked into blood from healthy volunteers. The subsequent isolation, DNA extraction, WGA, and qPCR analysis for BRAF mutations was not impeded by the presence of blood, and again the results matched that of the parental cells. (D) Isolation of CTCs from patients and subsequent genetic analysis for BRAF mutation status. These methods described above were was applied to blood samples from an additional cohort of patients, with CTCs isolated via capillary-based methods followed by DNA extraction, WGA, and qPCR analysis for BRAF. In each case, the BRAF mutation status of the isolated CTC corresponded to that of the primary tumor. qPCR amplification curves demonstrating strong amplification of the $BRAF^{V600E}$ allele in Patients W and Y, who were found to have mutated BRAF in the primary tumor. qPCR amplification curve of patient Z corresponds to the primary tumor's BRAF WT mutation status. Tabular data is also shown for the 4 patients from which individual CTCs were isolated and analyzed for BRAF mutation status.

FIGS. 5A-5E illustrate use of the NeuroInDx Kuiqpick system. FIG. 5A provides in vitro validation of capillary-based isolation of GFP probe-expressing cancer cells. Pre-collection [FIG. 5B] and post-collection [FIG. 5C] imaging of a target cell expressing GFP that is removed by capillary-based isolation (open circle). Disposable capillary unit (DCU) imaging (under phase contrast [FIG. 5D] and fluorescence [FIG. 5E, GFP] conditions) demonstrates the capture and isolation of a single cell.

FIG. 6A provides western blotting showing that BRAF protein ("Pan-RAF", top blot) is present in all cell lines. However, probing with an antibody specific for the mutated BRAF protein ("$BRAF^{V600E}$", middle blot) reveal that only A375P and Me1624 express the mutated protein. This data is consistent with sequencing results for each cell line as well as the subsequent WGA and qPCR analysis. Probing for β-actin served as a loading control. NSCLC=non-small cell lung cancer. FIG. 6B illustrates immunofluorescence staining of A375P (homozygous $BRAF^{V600E}$) and MeWo (homozygous BRAF WT) cell lines with DAPI and the $BRAF^{V600E}$ antibody, are consistent with the western blot and sequencing results. Bar, 30 um. FIG. 6C illustrates the results when the A375P cell line was incubated with the probe and DNA was extracted, amplified, and subject to qPCR analysis for the BRAF allele. PCR results demonstrated amplification of the $BRAF^{V600E}$ allele and absence of amplification of the BRAF WT allele. BRAF DNA was well-preserved despite cell exposure to the probe.

FIGS. 7A-7D illustrate detection of BRAF WT DNA in cells in culture and spiked into control blood. Each isolated melanoma cell analyzed for the $BRAF^{V600E}$ mutation qPCR analysis also underwent qPCR analysis using primers specific for BRAF WT. FIG. 7A illustrates the presence of the WT allele results in signal (Delta Rn, Y-axis) detectable by the $28^{th}$ cycle (as shown in the graph resulting from the BRAF WT kit control). FIG. 7B illustrates A375P (homozygous $BRAF^{V600E}$ mutated), Me1624 (heterozygous $BRAF^{V600E}$ mutated), and MeWo (homozygous BRAF WT) cells exposed to the probe, followed by capillary-based isolation, WGA, and qPCR analysis. In each case, the results of the qPCR analysis confirm the specific BRAF allele status of the parental cells in culture. FIG. 7C illustrates isolation and genetic analysis of melanoma cells spiked into control blood. Melanoma cells were prepared as in (B) but spiked into blood from healthy volunteers. The qPCR analysis demonstrated non-melanoma-specific BRAF WT amplification in each case. This is likely a result of WBCs co-isolating with cancer cells under the capillary-based cell collection protocol. FIG. 7D illustrates isolation of CTCs from patients and subsequent genetic analysis for BRAF mutation status. The qPCR analysis also demonstrated non-melanoma-specific BRAF WT amplification in each case. As in the case of melanoma cells spiked into control blood, the presence of BRAF WT DNA is likely due to normal WBCs co-isolating along with the cancer cells, and thus the WBC DNA also being co-amplified during WGA.

DETAILED DESCRIPTION OF THE INVENTION

Figure 2F:
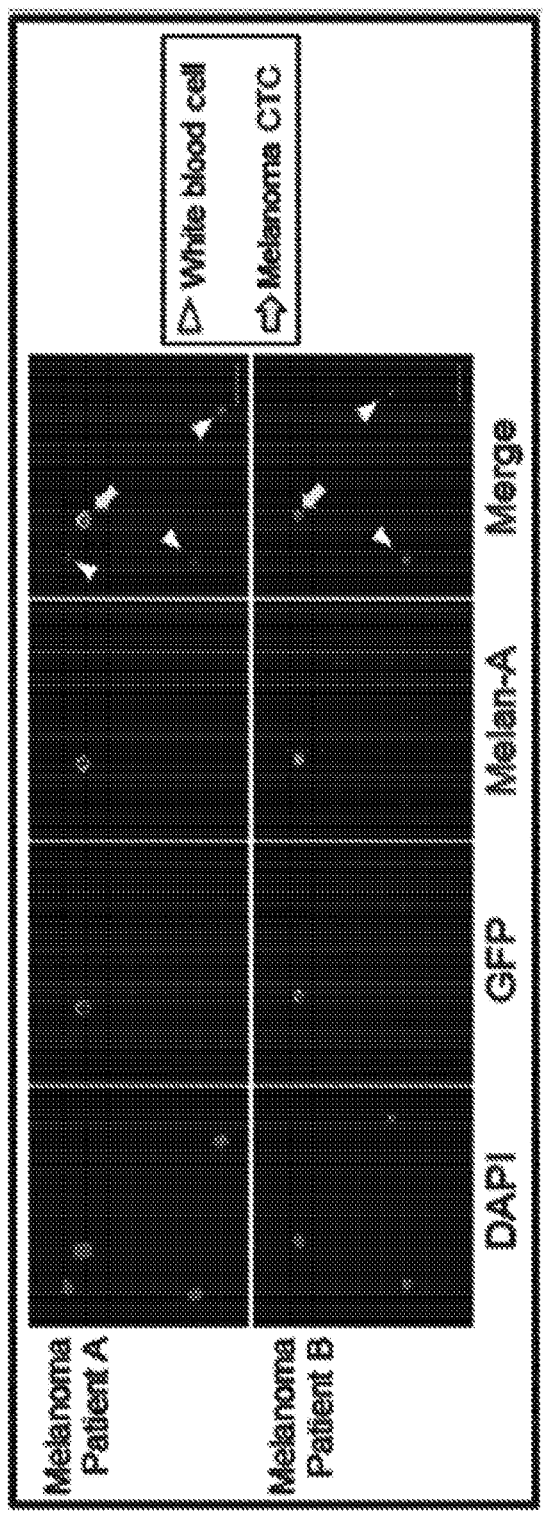

The present invention provides a telomerase-based assay not reliant on surface molecule expression (hereafter referred to as "the Assay"). Although is effective for detecting a tumor cells from a variety of sources, the assay is particularly useful in live circulating tumor cells.

In contrast to prior technologies which can only detect CTCs in epithelial cancers, the system described herein works for epithelial and non-epithelial cancers alike. In addition, the system described herein utilizes replication competent adenoviruses (also termed herein adenoviral probes). The replication competent adenoviruses provide quicker expression of a strong signal, typically by about 24 hours compared to the about 48 to about 72 hours needed for replication incompetent adenoviruses.

In the example below, the Assay's ability to identify melanoma cells in culture, CTCs in patients with melanoma, and mutant BRAF status was illustrated. To our knowledge, this is the first report of a telomerase-based assay for detecting and isolating melanoma CTCs. This Assay was effective in identifying melanoma cells in culture with high sensitivity and specificity. In patients with metastatic melanoma, the majority were found to have detectable CTC levels. Proof-of-principle data is reported demonstrating the feasibility of a novel capillary-based approach for isolating individual CTCs from patient samples, which may then be characterized for genetic mutations of therapeutic relevance. Together, these observations support the usefulness of the Assay.

While the Assay is not limited to this illustration, the example does demonstrate several advantages of this Assay including, live cell detection, and versatile and reliable CTC quantification. More particularly, as live cells are required for production of the detectable marker protein from adenovirus-infected cells, this Assay ensures that all detected CTCs are live. This is advantageous over assays using surface marker expression alone, which do not distinguish between cells which are live or dead at detection. Cells detected using this Assay may have greater biological significance and metastatic potential. With respect to quantification, the detectable signal (e.g., resulting from the probe) can be easily quantified using both flow cytometry and fluorescent microscopy, including coupling with automated or semi-automated computer image processing. This enables the establishment of parameters distinguishing CTCs from background noise on the basis of fluorescent intensity or size. In a further advantage, the vectors and methods described herein may optionally be integrated with existing CTC detection assays. For example, the replication-competent adenoviruses described herein can be designed to direct cancer cells to express other reporter proteins including other fluorescent proteins, enabling integration into different imaging and enrichment modalities and existing CTC analysis platforms. This Assay may also complement reverse transcriptase (RT)-polymerase chain reaction (PCR) assays, as it only requires isolation of the mononuclear layer and does not impede circulating DNA or mRNA analysis.

Adenoviral Vector Systems:

The methods described herein utilize at least one recombinant adenovirus which is designed to be preferentially express a detectable marker in live cells which are expressing telomerase, i.e., in replication competent circulating tumor or other cancer cells. The adenoviral vector system utilizes one or more replication-competent adenoviral particles, each of which particle has an adenoviral capsid into which is packaged an expression cassette which comprises at least a coding sequence for detectable marker protein.

Suitably, the adenovirus is designed to express functional E1a and/or E1b gene regions under the control of a tumor-specific promoter (e.g., a telomerase promoter). By "functional E1a", it is meant that a functional E1a protein is expressed; by "functional E1b", is meant that a functional E1b protein is expresses. Such a functional E1a and/or E1b region may be an intact E1 region may be located in its native location in the adenoviral genome or placed in the site of a deletion in the native adenoviral genome (e.g., in the E3 region). In one example of such a cassette, the E1a and/or E1b from the same adenovirus source as the capsid are expressed directly under the control of a human telomerase promoter, examples of which are provided below. In another example of such a cassette, the E1a and/or E1b from the same adenovirus source as the capsid are expressed indirectly under the control of a human telomerase promoter. In one example, a linker (e.g., an IRES) may be inserted between the E1a and E1b genes, so that a single promoter drives expression of both the E1a and E1b proteins. In one embodiment, the E1 gene region is from the same adenovirus type as the adenovirus which provides the capsid (e.g., an adenovirus type 5 ITR is used in an adenovirus type 5 capsid). In another embodiment, adenovirus is pseudotyped, i.e., the E1 gene region is replaced with a expression cassette containing the E1 gene region from a different adenovirus than the capsid, but which transcomplements the packaging of the nucleic acid molecule insert into an adenoviral capsid and replication. Examples of such transcomplementing adenovirus strains have been described in published patent documents and non-patent literature. See, e.g., WO 03/046124; WO 2005/001103; WO 2012/071318; WO2013/173702. See, also, discussion of adenoviruses in the passages herein relating to construction of adenoviral vectors.

Examples of telomerase-associated promoters, include, e.g., human telomerase reverse transcriptase (hTERT) [Lim, K. W., et al, Coexistence of two distinct G-quadruplex conformations in the hTERT promoter, J. Am. Chem. Soc. 132 (35), 12331-12342 (2010); U.S. Pat. No. 6,610,839], a human telomerase RNA (hTR), a hTERC promoter [Glasspool, R M, et al, "The hTERT and hTERC Telomerase Gene Promoters Are Activated by the Second Exon of the Adenoviral Protein, E1A, Identifying the Transcriptional Corepressor CtBP as a Potential Repressor of Both Genes", Neoplasia. 2005 June; 7(6): 614-622], and a progression elevated gene promoter (PEG-Prom) [See, e.g., US2004/0203066A1, for the sequences of the rat PEG-Prom promoter; Su Z Z, et al, Proc Natl Acad Sci USA. 2005 Jan. 25; 102(4):1059-64. Epub 2005 Jan. 12. "Targeting gene expression selectively in cancer cells by using the progression-elevated gene-3 promoter"].

The methods described herein may be performed with a single type of recombinant adenovirus with a heterologous E1 expression cassette or a mixture of different recombinant adenoviruses. For use in the methods described herein, the E1-expressing recombinant adenoviruses are engineered to further contain a second heterologous expression cassette in which a detectable marker such a fluorescent protein is expressed, in order to permit ex vivo or in vitro detection of a live cancer cell following infection with the adenovirus. Because the replication-competent adenoviruses replicate following infection of liver cancer cells, high levels of expression of a marker on the adenoviruses will be observed in those cells. In one embodiment, the second expression cassette may contain sequences encoding a tumor protein (e.g., EpCam) which are coexpressed with a detectable marker, such as a fluorescent protein. This permits the cancer cells which do not have useful cell surface markers to be detected visually through use of a marker (e.g., fluorescent) system and allows their capture using ligands for the marker and/or cell surface tumor antigen. The tumor protein may be fused to the marker, or the cassette may contain separate genes In some embodiments, reduction of an immune response to the vector may be accomplished by deletions in the E2b and/or DNA polymerase genes. The adenoviral vectors can also contain other mutations to the adenoviral genome, e.g., temperature-sensitive mutations or deletions in other genes.

The adenoviral vector systems are designed so that a reporter is expressed at high levels in the presence of live circulating tumor cells (CTCs), but not in the absence of such CTCs. In order to accomplish this, the adenoviral vector system is designed so that the reporter is expressed under the control of a promoter which is specifically activated in the present of CTCs. In one embodiment, the promoter a telomerase-associated promoter, such as are described herein. The telomerase-associated promoter drives E1 expression which is needed for viral replication, which in turn greatly augments amplification of vector and signal. Thus, the reporter protein may be expressed under the control of another promoter, including, e.g., a constitutive promoter, a tissue specific promoter, a tumor specific promoter, or the like.

In one embodiment, the reporter protein is a fluorescent protein. A variety of fluorescent proteins have been described in the literature. These proteins and their coding sequences are available from a variety of sources including commercial sources such as, e.g., BioVision, EMD Millipore, Invitrogen, amongst other sources. Suitable proteins include, green fluorescent protein, enhanced green fluorescent protein, mCherry, red fluorescent protein, and red fluorescent protein—turbo, amongst others. However, other suitable proteins may be selected.

| Fluorescent Proteins and Properties Thereof | | | | | | |
|---|---|---|---|---|---|---|
| Protein (Acronym) | Excitation Maximum (nm) | Emission Maximum (nm) | Molar Extinction Coefficient | Quantum Yield | in vivo Structure | Relative Brightness (% of EGFP) |
| GFP (wt) | 395/475 | 509 | 21,000 | 0.77 | Monomer* | 48 |
| Green Fluorescent Proteins | | | | | | |
| EGFP | 484 | 507 | 56,000 | 0.60 | Monomer* | 100 |
| Emerald | 487 | 509 | 57,500 | 0.68 | Monomer* | 116 |
| Superfolder GFP | 485 | 510 | 83,300 | 0.65 | Monomer* | 160 |

-continued

| Protein (Acronym) | Excitation Maximum (nm) | Emission Maximum (nm) | Molar Extinction Coefficient | Quantum Yield | in vivo Structure | Relative Brightness (% of EGFP) |
|---|---|---|---|---|---|---|
| Azami Green | 492 | 505 | 55,000 | 0.74 | Monomer | 121 |
| mWasabi | 493 | 509 | 70,000 | 0.80 | Monomer | 167 |
| TagGFP | 482 | 505 | 58,200 | 0.59 | Monomer* | 110 |
| TurboGFP | 482 | 502 | 70,000 | 0.53 | Dimer | 102 |
| AcGFP | 480 | 505 | 50,000 | 0.55 | Monomer* | 82 |
| ZsGreen | 493 | 505 | 43,000 | 0.91 | Tetramer | 117 |
| T-Sapphire | 399 | 511 | 44,000 | 0.60 | Monomer* | 79 |
| Blue Fluorescent Proteins | | | | | | |
| EBFP | 383 | 445 | 29,000 | 0.31 | Monomer* | 27 |
| EBFP2 | 383 | 448 | 32,000 | 0.56 | Monomer* | 53 |
| Azurite | 384 | 450 | 26,200 | 0.55 | Monomer* | 43 |
| mTagBFP | 399 | 456 | 52,000 | 0.63 | Monomer | 98 |
| Cyan Fluorescent Proteins | | | | | | |
| ECFP | 439 | 476 | 32,500 | 0.40 | Monomer* | 39 |
| mECFP | 433 | 475 | 32,500 | 0.40 | Monomer | 39 |
| Cerulean | 433 | 475 | 43,000 | 0.62 | Monomer* | 79 |
| mTurquoise | 434 | 474 | 30,000 | 0.84 | Monomer* | 75 |
| CyPet | 435 | 477 | 35,000 | 0.51 | Monomer* | 53 |
| AmCyan1 | 458 | 489 | 44,000 | 0.24 | Tetramer | 31 |
| Midori-Ishi Cyan | 472 | 495 | 27,300 | 0.90 | Dimer | 73 |
| TagCFP | 458 | 480 | 37,000 | 0.57 | Monomer | 63 |
| mTFP1 (Teal) | 462 | 492 | 64,000 | 0.85 | Monomer | 162 |
| Yellow Fluorescent Proteins | | | | | | |
| EYFP | 514 | 527 | 83,400 | 0.61 | Monomer* | 151 |
| Topaz | 514 | 527 | 94,500 | 0.60 | Monomer* | 169 |
| Venus | 515 | 528 | 92,200 | 0.57 | Monomer* | 156 |
| mCitrine | 516 | 529 | 77,000 | 0.76 | Monomer | 174 |
| YPet | 517 | 530 | 104,000 | 0.77 | Monomer* | 238 |
| TagYFP | 508 | 524 | 64,000 | 0.60 | Monomer | 118 |
| PhiYFP | 525 | 537 | 124,000 | 0.39 | Monomer* | 144 |
| ZsYellow1 | 529 | 539 | 20,200 | 0.42 | Tetramer | 25 |
| mBanana | 540 | 553 | 6,000 | 0.7 | Monomer | 13 |
| Orange Fluorescent Proteins | | | | | | |
| Kusabira Orange | 548 | 559 | 51,600 | 0.60 | Monomer | 92 |
| Kusabira Orange2 | 551 | 565 | 63,800 | 0.62 | Monomer | 118 |
| mOrange | 548 | 562 | 71,000 | 0.69 | Monomer | 146 |
| mOrange2 | 549 | 565 | 58,000 | 0.60 | Monomer | 104 |
| dTomato | 554 | 581 | 69,000 | 0.69 | Dimer | 142 |
| dTomato-Tandem | 554 | 581 | 138,000 | 0.69 | Monomer | 283 |
| TagRFP | 555 | 584 | 100,000 | 0.48 | Monomer | 142 |
| TagRFP-T | 555 | 584 | 81,000 | 0.41 | Monomer | 99 |
| DsRed | 558 | 583 | 75,000 | 0.79 | Tetramer | 176 |
| DsRed2 | 563 | 582 | 43,800 | 0.55 | Tetramer | 72 |
| DsRed-Express (T1) | 555 | 584 | 38,000 | 0.51 | Tetramer | 58 |
| DsRed-Monomer | 556 | 586 | 35,000 | 0.10 | Monomer | 10 |
| mTangerine | 568 | 585 | 38,000 | 0.30 | Monomer | 34 |
| Red Fluorescent Proteins | | | | | | |
| mRuby | 558 | 605 | 112,000 | 0.35 | Monomer | 117 |
| mApple | 568 | 592 | 75,000 | 0.49 | Monomer | 109 |
| mStrawberry | 574 | 596 | 90,000 | 0.29 | Monomer | 78 |
| AsRed2 | 576 | 592 | 56,200 | 0.05 | Tetramer | 8 |
| mRFP1 | 584 | 607 | 50,000 | 0.25 | Monomer | 37 |
| JRed | 584 | 610 | 44,000 | 0.20 | Dimer | 26 |
| mCherry | 587 | 610 | 72,000 | 0.22 | Monomer | 47 |
| HcRed1 | 588 | 618 | 20,000 | 0.015 | Dimer | 1 |
| mRaspberry | 598 | 625 | 86,000 | 0.15 | Monomer | 38 |
| dKeima-Tandem | 440 | 620 | 28,800 | 0.24 | Monomer | 21 |

Fluorescent Proteins and Properties Thereof

| Protein (Acronym) | Excitation Maximum (nm) | Emission Maximum (nm) | Molar Extinction Coefficient | Quantum Yield | in vivo Structure | Relative Brightness (% of EGFP) |
| --- | --- | --- | --- | --- | --- | --- |
| HcRed-Tandem | 590 | 637 | 160,000 | 0.04 | Monomer | 19 |
| mPlum | 590 | 649 | 41,000 | 0.10 | Monomer | 12 |
| AQ143 | 595 | 655 | 90,000 | 0.04 | Tetramer | 11 |

*Weak Dimer

In yet another embodiment, the vector system expresses a fusion protein which comprises a protein, polypeptide or peptide fused in frame (directly or via a spacer or linker) to a fluorescent protein or a polypeptide or peptide thereof which functions (i.e., fluoresces) in the cell (this is termed a "functional fragment"). In one embodiment, the fusion partner for the fluorescent protein or functional fragment thereof is an epithelial cell adhesion molecule such as EpCAM. Alternatively, another tumor-associated cell surface marker may be selected. See, e.g., the Human Potential Tumor Associated Antigen database (HPtaa) [http://www.hptaa.org and: HPtaa database-potential target genes for clinical diagnosis and immunotherapy of human carcinoma. Wang X S, Zhao H T, Xu Q W, et al. Nucleic Acids Res. 2006 Jan. 1: 34 (Database issue):D607-12]. van der Bruggen P, Stroobant V, Vigneron N, Van den Eynde B. Peptide database: T cell-defined tumor antigens. Cancer Immun 2013. URL: http://www.cancerimmunity.org/-peptide/] and database of T cell-defined human tumor antigens: the 2013 update. Fusion proteins may be constructed using techniques such as described in C. Y. Wang, et al, 2004 November; 20(6): 765-768; K. Slanchev et al, PLoS Genet 2009. The vector system provides a sequence encoding a reporter which is expressed directly or indirectly under the control of a telomerase-specific promoter. The expression cassette with the reporter coding sequence also may contain other regulatory control sequences necessary for expression of the reporter protein, including, e.g., an enhancer, a polyA, amongst other elements.

An adenovirus may contain a reporter gene expression cassette located in the E1 region downstream of the E1 expression cassette, and contain one or more deletions in the immediately early gene regions (e.g., E3 which is not required for replication or packaging), or another immediately early gene region which is required to be supplied during packaging (e.g., by another vector or by the host cell). The reporter sequence may be located in the site of a deleted adenovirus early gene region, e.g., E2a, E3, or E4a. Optionally, two more reporter gene expression cassettes located either in tandem or in different adenovirus early gene sites (e.g., both in E3) of a single recombinant adenovirus vector. However, other arrangements in the adenovirus may be engineered by one of skill in the art utilizing known genetic engineering and recombinant techniques.

In one embodiment, the fluoro-protein cassette is under the control of a constitutive promoter which drives its expression. In one embodiment, the promoter is a strong constitutive promoter, e.g., the CAGS promoter, which composed of the chicken β-actin promoter with human cytomegalovirus immediate early (CMVIE) enhancer. Examples of constitutive promoters include, without limitation, the TBG promoter, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen]. A number of other expression control sequences, including promoters which are native, tissue-specific, tumor-associated, or inducible, or others which are known in the art and may be utilized. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art.

Other expression control sequences may include appropriate transcription initiation, termination, promoter and enhancer sequences; efficient RNA processing signals such as splicing and polyadenylation (polyA) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used. One can enhance expression of desired proteins by known means to enhance the effectiveness of this system. For example, using the Woodchuck Hepatitis Virus Posttranscriptional Regulatory Element (WPRE). In a further embodiment, other expression control elements, such as enhancer elements, polyadenylation sites or Kozak consensus sequences may be used.

III. Production of Replication-Competent Adenoviruses

Adenoviral vectors may be produced using methods which are known in the art, e.g., through use of adenoviral plasmids. The particle is composed of an adenoviral capsid which directs targeting of the adenoviral vector. Because this assay is performed in vitro, limitations on in vivo use of adenoviruses based on pre-existing immunity in the patient population to the adenovirus capsid (and particularly the capsid) are not a factor in the selection of the adenovirus source for the vectors described herein. Rather, adenoviruses are selected taking into consideration such factors as ease of production and ability to target and infect cells efficiently. In the examples described herein, is adenovirus is human adenovirus 5 [VR-5, American Type Culture Collection]. However, an adenovirus from another source, particularly those naturally or modified to have particular affinity for circulating tumor cells in mammals, including humans, may be readily selected. Such an adenovirus may be of human origin, including, without limitation, Ad2, Ad31, Ad36 and Ad37. In other embodiments, the adenovirus may be of simian or another animal origin. Examples of suitable simian adenoviruses include those described in, e.g., U.S. Pat. No. 8,105,574 (Pan5, Pan6, Pan7, SV1, SV25, SV39), WO 2012/071318 (A1321, A1325, A1295, A1316, A1322), WO 03/046124; WO2005/001103; WO2012/071318; WO 2013/

173702; WO 2009/073104; WO 2009/105084; and WO 2009/073102. Still other adenoviruses are known and may be obtained from a variety of sources including the ATCC, commercial and academic sources, or the sequences of the Ad may be obtained from GenBank or other suitable sources. The adenoviral vectors can also contain other mutations to the adenoviral genome, e.g., temperature-sensitive mutations or deletions in other genes.

Thus, one embodiment, the system incorporates a vector in which the viral sequences contain mutation that renders it temperature sensitive. At the lower "permissive" temperature of 32° C., the virus is able to replicate within transduced cells and thus amplify the fluorescent signal. However, before the replication process can proceed to cell lysis (and thus death of the transduced CTC), the cells are shifted to the higher "non-permissive" temperature of 37° C. At that higher temperature, all replication ceases and the CTCs should stay intact.

A range of adenovirus nucleic acid sequences can be employed in the vectors. As described herein, the adenoviruses are designed to remain replication competent, i.e., by retaining a functional E1a and/or E1b region in the adenoviral vectors. By "functional E1a", it is meant that a functional E1a protein is expressed; by "functional E1b", is meant that a functional E1b protein is expresses. Such a functional E1a and/or E1b region may be an intact E1 region may be located in its native location in the adenoviral genome or placed in the site of a deletion in the native adenoviral genome (e.g., in the E3 region). All or a portion of the adenovirus delayed early gene E3 may be eliminated from the adenovirus sequence which forms a part of the recombinant virus. The function of an E3 is believed to be irrelevant to the function and production of the recombinant virus particle. Adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the adenovirus genome. Similarly, deletions in the intermediate genes IX and IVa$_2$ may be useful for some purposes. Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination.

An adenoviral vector lacking any essential adenoviral sequences (e.g., E2a, E2b, E4 ORF6, L1, L2, L3, L4 and L5) may be cultured in the presence of the missing adenoviral gene products which are required for viral infectivity and propagation of an adenoviral particle. Although less desired, certain embodiments may utilize E1a, or E1b, deleted adenoviruses. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application WO96/13597, published May 9, 1996, and incorporated herein by reference.

1. Helper Viruses

Thus, depending upon the adenovirus gene content of the viral vectors employed to carry the expression cassette, a helper adenovirus or non-replicating virus fragment may be necessary to provide sufficient adenovirus gene sequences necessary to produce an infective recombinant viral particle containing the expression cassette(s). Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 374: 16985-16987 (1989); K. J. Fisher and J. M. Wilson, *Biochem. J.*, 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Complementation Cell Lines

To generate recombinant adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the Ad vector. This is particularly advantageous because, due to the diversity between the Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products that can be utilized for production of an E1-deleted adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene from the same adenovirus as supplies the adenoviral vector capsid or a transcomplementary adenovirus under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired adenoviral gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), *Hum Gene Ther*, 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

3. Assembly of Viral Particle and Transfection of a Cell Line

Generally, when delivering a vector for production of the adenoviral particle, the adenoviral vector is delivered in an amount from about 5 µg to about 100 µg DNA, and preferably about 10 to about 50 µg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

The packaging or production vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired expression cassette-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. However, the invention is not limited to the method for production of the adenoviral vectors.

The resulting adenoviruses are useful in the methods of the system and assay of invention.

Tumor Cell Detection and Isolation:

The invention utilizes one or more of the replication-competent adenoviruses described herein which preferentially express a fluorescent protein in the presence of live circulating tumor cells to qualitatively and quantitatively detect the presence of CTCs.

As described above, the method for detecting circulating tumor cells ex vivo involves combining a test sample from a patient suspected of having circulating tumor cells and an adenoviral system in a well, tube or another vessel containing media sufficient to permit infection of the cells and sustain the cells throughout the assay period.

The test sample and the adenoviral system are incubated under conditions which permit cell infection and which permit expression of the reporter protein. The cell media may be replaced or replenished as needed throughout this process. The assay utilizes an adenoviral vector (alternatively referred to herein as a "probe"), which is a replication-competent adenovirus. In one embodiment, the adenovirus has the E1 region which controls replication regulated by the hTERT promoter element. A downstream promoter activates fluorescent marker protein production. Thus, a cell with active telomerase activity produces increasing copies of the virus leading to amplified marker protein expression detectable by fluorescence microscopy or another suitable device or technique.

After the desired incubation period, reporter protein expression is measured in the test samples. Measurements may be taken at a single time point or at multiple time points. Typically, expression of the reporter protein is measured at about eighteen to seventy-two hours, or about 20 to about 48 hours, or about 24 to about 35 hours, after first combining the adenoviral system and the test sample. However, other suitable times may be selected. Suitably, these measurements may be taken visually or through an automated or semi-automated system without disrupting the cells. [See, e.g., R Yaron, et al, "A convenient, optimized pipeline for isolation, fluorescence microscopy and molecular analysis of live single cells, Biological Procedures Online 2014, 16:9 doi:10.1186/1480-9222-16-9, a complete electronic version of this article can be found online at: http://www.biologicalproceduresonline.com/content/16/1/9; M. Fero and K. Pogliano, "Automated Quantitative Live Cell Fluorescence Microscopy", CSH Perspectives in Biology, http://cshperspectives.cship.org/content/2/8/a000455 (published in advance Jun. 30, 2010); and commercially available systems, e.g., available from Leica Microsystems; Life Technologies; Nikon MicroscopyU]. In this manner, cells expressing the marker protein may be counted (enumerated). Where two marker proteins are expressed, cells expressing both markers or only a single marker may be counted and distinguished from one another. Optionally, both populations of cells may be collected, or only a single population of cells may be collected for more detailed analysis. This ability to collect these tumor cells permits tracking of resistance of a targeted therapy. For example, the methods described herein may be used for samples from patients who have undergone a relapse or recurrent tumor, who have a residual resistant tumor, or otherwise have shown resistance to treatment. Alternatively, this method may be used to assist in selection of a treatment (primary or secondary) for a subject by identifying the genomic mutation associated with the patient's tumor, and in one embodiment, for identifying the gene associated with development of resistance.

The cells expressing the marker protein may be collected. Collection may be by any suitable technique. In one embodiment, the adenovirus-infected CTC expressing the marker (fluorescent) protein are captured using a ligand specific to said protein.

In one embodiment, the ligand is an antibody. As used herein, unless otherwise specified, an "antibody" (e.g., targeted to a fluorescent protein) refers to a full-length immunoglobulin or a functional fragment thereof which specifically binds to its selected target. Functional fragments may include, e.g., an immunoglobulin portion which binds a target (e.g., marker protein or antigen). Examples of functional fragments may include, e.g., a Fab fragment, a monovalent fragment consisting of the VL, VH, CL and CH I domains; a F(ab')2 fragment, a bivalent fragment comprising two Fab fragments linked by a disulfide bridge at the hinge region; a Fd fragment consisting of the VH and CH1 domains; a Fv fragment which is the VL and VH domains of a single arm of an antibody, a dAb fragment which is a VH domain; single chain antibodies, such as diabodies are also encompassed. Still further, an antibody or functional fragment thereof a larger immunoadhesion molecules, formed by covalent or noncovalent association of the antibody or antibody portion with one or more other proteins or peptides. The antibody may be from any class of immunoglobulins, including IgM, IgG, IgD, IgA and IgE, and any isotype, including IgG1, IgG2, IgG3 and IgG4.

A variety of antibodies are commercially available which are specific for such marker proteins. Suitable sources may include, e.g., Amalgaam, Sigma-Aldrich, Clontech, and provides of the fluorescent proteins, see, e.g., anti-green fluorescent protein antibodies (Ayes Labs, Inc., Life Technologies; Rockland Immunochemicals]; anti-cyan fluorescent protein [Clontech].

Optionally, the antibody may be bound to a solid support, e.g., a column or conjugated or bound to a bead which allows for ready capture and purification. In one embodiment, the bead is magnetic. In such an embodiment, the subsequent application of a strong magnet will pull down the beads along with the tumor cells, whereas normal cells will be washed away. Thus, the CTC may be collected using column chromatography or other suitable techniques. See, e.g., Yu et al, Circulating tumor cells: approaches to isolation and characterization, J Cell Biol., 192 (3): 373-382 (Feb. 7, 2011). Following collection, total genomic DNA may be extracted, amplified, purified and analyzed for a tumor associated mutation. Methods for single cell whole genome amplification have been described in the literature and kits for doing same are commercially available (e.g., from Yikon Genomics; Qiagen; and Sigma-Aldrich).

In one embodiment, an adenoviral probe system uses a combination of vectors. In one embodiment, the vector system utilizes is first probe which has an adenoviral human type 5 capsid (H5), which has a deletion in the E3 coding region, but has E1 sequences under control of an hTERT promoter, and further having an expression cassette for a fluorescent protein inserted therein. For example, H5'0.040.hTERT.E1a.IRES.E1b.pA.CB7.CI. pCherry.WPRE.bGH, is replication-competent adenovirus, in which the native E1 promoter is replaced with an hTERT promoter, and an IRES is cloned between the E1a and E1b coding regions such that the expression of E1b is also controlled by the tumor-specific promoter, followed by a polyA signal at the end of the E1 expression cassette. A second expression cassette is also packaged into the adenoviral genome, which contains a chicken beta actin promoter, the pCherry coding sequences, a woodchuck post-regulatory element, and the bovine growth hormone polyA sequence. This vector may be used in combination with a second adenoviral vector which is also E3-deleted and has the native E1a promoter replaced with the hTERT promoter, and which is further engineered to express both a first marker protein and a fusion protein comprising EpCAM fused to a second marker protein. An illustrative vector expresses the CherryPicker (CP) and EpCAM-TurboGFP (EG) proteins from H5'0.040.hTERT.E1a.IRES.E1b.pA.CB7.CI.EpCAM.WPRE.bGH. The CP protein is fluorescent, thus enabling detection of CTC, but is also capable of being captured and enriched by antibodies designed against CP ("anti-CP antibodies"). Anti-CP antibodies in turn can be conjugated or bound to magnetic beads, thus enriched. Patient blood samples which have been exposed to the first probe can be subsequently exposed to anti-CP-conjugated magnetic beads. The tumor cells will preferentially express CP due to the presence of elevated telomerase activity whereas normal cells will be unaffected. The tumor cells will then bind to the anti-CP-conjugated magnetic beads. The subsequent application of a strong magnet will pull down the beads along with the tumor cells, whereas normal cells will be washed away. All the above steps can be repeated with vectors designed to contain different marker proteins and methods utilizing ligands designed specifically for those marker proteins. Variations on this combination and capture method will be readily appreciated by one of skill in the art.

The Assay protocol is as follows: a biological fluid such as peripheral blood (other biological fluids such as whole blood, arterial blood, cerebrospinal fluid, peritoneal or pleural fluid, etc.) is collected in a tube containing a clot inhibitor (such as sodium heparin or EDTA), cooled, and processed within hours of collection (e.g., within about two hours, although longer or shorter times may be selected). The biological fluid (such as peripheral blood) is combined with a substantially equivalent amount of sterile phosphate-buffered saline (PBS) and introduced into an OncoQuick tube (Greiner Bio-One, Frickenhausen, Germany) or suitable alternative. After centrifugation of the tube, the buffy coat containing CTCs and the remaining white blood cells (WBCs) are isolated and added to wash buffer (0.5% bovine serum albumin [BSA] in 1×PBS) for a second centrifugation step. The supernatant is discarded until about 500 µL of solution remains. The remaining cells are re-suspended in 900 µL of media (such a DMEM (Invitrogen, Carlsbad, Calif.) supplemented with 10% FBS (Invitrogen, Carlsbad, Calif.) and 1.0% penicillin-streptomycin or can be any other media preparations that foster the survival of the cells). The cells are split evenly into wells of an Poly-D-lysine chamber slide and incubated at 37° C. in an atmosphere of 5% $CO_2$. All samples are incubated with viral particles (such as $2\times10^8$ per 750 µL of volume but can varied to customize to the activity and purity of the virus and its preparation. At about 24, about 48, and about 72 hours, the chamber slide is removed from the incubator and imaged using a computer-automated imaging program, such as, e.g., Image Pro Plus 7.0, Media Cybernetics, Rockville, Md. The program can filter images by intensity, size, and other criteria to identify and enumerate marker protein expressing cells. Other image acquisition and analysis software programs can also be utilized for distinguishing and enumerating cells.

The selected isolation of cells can be performed using a capillary-based vacuum-assisted cell acquisition system (Kuigpick™, NeuroInDx) [Kudo L C, et al., Novel cell and tissue acquisition system (CTAS): Microdissection of live and frozen brain tissues. PLoS One. 2012; 7(7):e41564] or a suitable alternative system. Other systems can be employed to isolate the virus-identified tumor cells, such as DEPArray™ technology marketed by Silicon Biosystems, in which rare cells suspended in a liquid can be moved by electrokinetic forces exerted via an array of electrodes in a process called dielectrophoresis (DEP). Calibration may be initially performed under bright field conditions, followed by the collection of individual fluorescent cells via fluorescence microscopy. Total genomic DNA is extracted and amplified using Single Cell Whole Genome Amplification Kit (Yikon Genomics Co. Ltd, Taizhou, China) [Zong C, et al, *Science*. 2012; 338(6114):1622-1626] or a suitable alternative. After genomic DNA amplification, PCR products are purified using Agencourt® AMPure®XP kit (Beckman Coulter, Brea, Calif.). Amplified and purified genomic DNA from collected cells may then be analyzed using eQ-PCR™ BRAF Detection Kit (TrimGen Corporation, Sparks, Md.) and subsequently sequenced. The purified DNA may be analyzed for a genetic mutation.

In a further embodiment, the invention provides a product comprising a vector system for use in a telomerase based assay for isolating circulating tumor cells ex vivo or in vitro.

The product may contain one or more adenoviral particles, optionally in freeze-dried state; a suspending agent; tubes, pouches, vials, syringes, slide(s), well plate(s), ligands for a marker (fluorescent) protein, diluents, suspending agents, or other suitable components of a kit. The ligand(s) for the marker may optionally be bound to a magnetic bead or other solid support, which may also be provided with the product or kit.

The words "comprise", "comprises", "comprising", "contain", "contains" and "containing" are to be interpreted inclusively rather than exclusively. The works "consist", "consisting", and its variants, are to be interpreted exclusively, rather than inclusively.

As used herein in reference to numeric values provided herein, the term "about" may indicate a variability of as much as 10% unless otherwise specified.

The following examples are illustrative of embodiments of the invention and do not limit the scope of the invention.

Example 1: Telomerase-Based Assay for Detecting and Isolating Live Melanoma CTCs In the following example, microcapillary dissection techniques are to "pluck out" individual CTCs, from which DNA is extracted, amplified (via whole genome amplification (WGA)), and accessed via quantitative PCR for specific DNA mutations of therapeutic relevance.

The assay utilizes an adenoviral vector that, in the presence of elevated human telomerase activity, drives the amplification of green fluorescent protein (GFP). Tumor cells are then identified via an image processing system. The assay was tested on melanoma cells in culture or spiked into control blood, and on samples from patients with metastatic melanoma. Genetic analysis of the isolated melanoma CTCs was then performed for BRAF mutation status.

In summary, the assay was effective for all melanoma cell lines tested with sensitivity of 92% (95% confidence index (CI): 84.4-99.1%) and specificity of 99% (95% CI: 99.8-99.9%). In a pilot trial of patients with metastatic disease, CTCs were identified in 9 of 10 patients, with a mean of 6.0 CTCs/mL. At a cutoff of 1.1 CTCs/mL, the assay exhibits test performance of 90.0% sensitivity and 91.7% specificity. BRAF mutation analysis of melanoma cells isolated from culture or spiked control blood, or from pilot patient samples was found to match the known BRAF mutation status of the cell lines and primary tumors.

These promising findings support further studies, including towards integrating into the management of patients with melanoma receiving combination therapy.

A. Materials and Methods

1. Cell Culture

Me1624, C8161, and A375P melanoma cells were maintained in Roswell Park Memorial Institute medium (RPMI-1640, Invitrogen, Carlsbad, Calif.) supplemented with 10% fetal bovine serum (FBS, Invitrogen, Carlsbad, Calif.) and 1.0% penicillin-streptomycin at 37° C. in an atmosphere of 5% $CO_2$, while MeWo cells were maintained in Eagle's Minimal Essential Media (MEM, Mediatech, Inc, Manassas, Va.) supplemented with 10% FBS (Invitrogen, Carlsbad, Calif.) and 1.0% penicillin-streptomycin at 37° C. in an atmosphere of 5% $CO_2$. U251 glioblastoma cells were grown in Dulbecco's modified Eagle's medium (DMEM, Invitrogen, Carlsbad, Calif.) with 10% FBS (Invitrogen, Carlsbad, Calif.) and 1.0% penicillin-streptomycin at 37° C. in an atmosphere of 5% CO2. Hoechst staining (Invitrogen, Carlsbad, Calif.) was used for live cell counting.

2. Western Analysis

Cells were harvested by scraping, centrifugation, and lysis on ice for 2 hours. Samples were then subject to electrophoresis, transferred to PVDF membranes and blocking against non-specific binding. The following antibodies were employed for specific protein detection: Pan-RAF (1:2000, mouse mAb, Cell Signaling Technology, Danvers, Mass.), $BRAF^{V600E}$ (1:2000 mouse mAb, NewEast Biosciences, King of Prussia, Pa.), and β-actin (1:10,000, rabbit mAb, Cell Signaling Technology, Danvers, Mass.). Following incubation with the primary antibody, the membranes was rinsed with TBST, incubated for 5 minutes with horse radish peroxidase-conjugated secondary antibody, washed further with TBST, and finally developed with the Amersham Enhanced Chemiluminescence (ECL) kit or ECL Prime western blotting detection system (GE Healthcare, Little Chalfornt UK).

3. CTC Assay

The assay utilizes an adenoviral probe (referred to as the "probe"), which is a replication-competent adenovirus whose replication is regulated by the hTERT promoter element. A downstream CMV promoter activates GFP production. Thus, a cell with active telomerase activity produces increasing copies of the virus leading to amplified GFP expression detectable by fluorescence microscopy. The initial probe utilized in the studies was obtained from Oncolys BioPharma [Japan].

The Assay protocol is as follows: up to 10 mL of peripheral blood is collected in a sodium heparin tube, placed on ice, and processed within two hours of collection. The whole blood is combined with 10 mL of sterile phosphate-buffered saline (PBS) and introduced into an OncoQuick tube (Greiner Bio-One, Frickenhausen, Germany). After centrifugation of the OncoQuick tube, the buffy coat containing CTCs and the remaining WBCs are isolated and added to wash buffer (0.5% bovine serum albumin [BSA] in 1×PBS) for a second centrifugation step. The supernatant is discarded until 500 uL of solution remains. The remaining cells are re-suspended in 900 uL DMEM (Invitrogen, Carlsbad, Calif.) supplemented with 10% FBS (Invitrogen, Carlsbad, Calif.) and 1.0% penicillin-streptomycin. The cells are split evenly into two wells of an 8 well Poly-D-lysine chamber slide and incubated at 37° C. in an atmosphere of 5% $CO_2$. All samples are incubated with $2×10^8$ viral particles per 750 µL of volume. At 24, 48, and 72 hours, the chamber slide is removed from the incubator and imaged using a computer-automated imaging program (Image Pro Plus 7.0, Media Cybernetics, Rockville, Md.). The program can filter images by intensity, size, and other criteria to identify and enumerate GFP expressing cells.

4. Determination of Probe's Sensitivity and Specificity for Melanoma Cells

Melanoma cell lines were exposed to the probe and imaged at 24, 48, and 72 hours to quantify GFP expression induced over time. Hoechst stain was added to cells prior to imaging to identify all viable cells on the plate. The GFP and Hoechst signal was enumerated for each well and sensitivity calculations were done for three cell lines. Healthy control blood was processed using Assay protocols and specificity determined by the ratio of false positive signal to total number of WBCs in each plate.

Scatterplots displaying each detected cell by size and GFP intensity were obtained. Using stringent GFP intensity parameters (black dotted line, FIG. 2B), false positive WBC signals are able to be further excluded.

5. Immunofluorescence Staining

Melanoma cells grown in vitro were seeded on 8 well Poly-D-lysine chamber slides. Patient samples undergoing immunofluorescence staining were prepared according to the Assay protocol described above. Samples were fixed by media aspiration, PBS rinse followed by 4% formaldehyde fixation (15 minutes in room temperature), permeabilization with 0.25% Triton X-100 (10 minutes at room temp) followed by 2-3 washes with PBS, 5 minutes each. Samples were incubated with Melan-A antibody (1:50 mouse mAb, Santa Cruz Biotechnology, Dallas, Tex.) or $BRAF^{V600E}$ antibody (1:200 mouse mAb, NewEast Biosciences, King of Prussia, Pa.). Samples were incubated with 1:200 chicken anti mouse-Alexa fluor (594) (Invitrogen, Grand Island, N.Y.) for 1 hour at room temp. The cells were mounted with the media containing DAPI and then imaged using fluorescence microscopy. All the steps were followed by 3 washing steps with PBS, 5 minutes each.

6. Cellular Isolation for Genetic Analyses

The selected isolation of cells was performed using a capillary-based vacuum-assisted cell acquisition system (Kuigpick™, NeuroInDx) [Kudo L C, et al., Novel cell and tissue acquisition system (CTAS): Microdissection of live and frozen brain tissues. PLoS One. 2012; 7(7):e41564]. Calibration was initially performed under bright field conditions, followed by the collection of individual fluorescent cells via fluorescence microscopy. Total genomic DNA was extracted and amplified using Single Cell Whole Genome Amplification Kit (Yikon Genomics Co. Ltd, Taizhou, China) [Zong C, et al, *Science.* 2012; 338(6114):1622-1626]. After genomic DNA amplification, PCR products were purified using Agencourt® AMPure®XP kit (Beckman Coulter, Brea, Calif.). Amplified and purified genomic DNA from collected cells were then analyzed using eQ-PCR™ BRAF Detection Kit (TrimGen Corporation, Sparks, Md.) and subsequently sequenced. The purified DNA was analyzed for the BRAF mutations by Shifted Termination Assay (STA) using the Mutector™ kit (TrimGen Corporation, Sparks, Md., USA) [Lin J, et al., Br J Cancer. 2011; 104(3):464-468; Kang S Y, et al, Diagn Pathol. 2013; 8(1):121].

7. Pilot Study and Control Blood Samples

In partnership with the Institution's Cancer Center, which runs an IRB-approved melanoma biobank protocol, blood samples from consenting patients with metastatic melanoma were collected for biomarker analysis. After completion of sample processing, de-identified patient demographics and disease course details were provided for statistical analysis.

Healthy subjects without prior history of cancer and between ages 18-60 were consented to blood draws of up to 20 mL on an IRB-approved control blood study. For cell spiking experiments, 500 cells (Nexcelom Biosciences' Cellometer, Lawrence, Mass.) were added to the blood sample prior to sample processing.

8. Statistical Analysis

Statistical analysis was done with the STATA program (StataCorp, College Station, Tex.). Descriptive statistics were used for sensitivity and specificity analysis. ANOVA and linear regression models were used to analyze CTC counts with patient data from the pilot study. Univariate and multivariable analysis was done to establish associations between binary variables (e.g. sex, BRAF WT vs mutant) and CTC counts as a continuous outcome variable. Receiver operator characteristic (ROC) curves were generated using data from blood samples of healthy volunteers and patients with known melanoma.

B. Results

1. Melanoma Cells in Culture and in Patients are Identified by the Telomerase-Detecting Fluorescent Probe The high levels of telomerase activity in melanoma cells translated to strong expression of fluorescence after exposure to the probe and did not interfere with Melan-A expression (FIG. 1A). The probe resulted in strong fluorescence in melanoma cells regardless of BRAF WT (left panel) or mutant (right panel) status, and with peak fluorescence reached by 48 hours (FIG. 1B). The probe had a high sensitivity for melanoma cells 91.8% (95% CI: 84.4-99.1%), which was also comparable to other tumors in which the probe has been found to be effective using other methods.

These encouraging results enabled the integration of the probe with a semi-automated, computer-driven image acquisition and analysis system (FIG. 2A). This system has been described in previous publications and incorporates reproducible cell identification and imaging as well as filters for size and fluorescence so that that cellular debris and cells with weak fluorescence are excluded from analysis [Ju M, et al. Cancer Biol Ther. 2014; 15(6); MacArthur K M, et al. Cancer Res. 2014; 74(8):2152-2159; Dorsey J, et al. Tracking viable circulating tumor cells (CTCs) in the peripheral blood of non-small cell lung cancer patients undergoing definitive radiation therapy: Pilot study results. Cancer. 2014]. As an additional validation step prior to testing patient samples, control experiments were performed in which peripheral blood samples from healthy volunteers were spiked with or without melanoma cells and exposed to the probe. Control blood showed minimal fluorescence (specificity of 99.9% [95% CI: 99.8%-99.9%]) while melanoma cells were readily detected with high sensitivity against the background of normal blood cells (FIG. 2B).

2. Pilot Study of the Assay in Patients with Metastatic Melanoma

Having validated the Assay for detection of melanoma cells, a pilot study was initiated in patients with metastatic melanoma. After exposure to the probe, patient samples were imaged and readily amenable to software analysis, with individual melanoma cells identified in peripheral blood samples after filters for cell size and fluorescence were applied (FIG. 2B, right-most panel). In contrast to cultured melanoma cells, ex vivo melanoma CTCs tend not to extend their cytoplasm to create pseudopods, thus appearing slightly smaller. As further confirmation of melanoma cells detected by the probe, counterstaining for Melan-A was performed in the patient blood samples after analysis. Expression of Melan-A coincided with the green fluorescence protein (GFP) in melanoma cells, while white blood cells showed neither GFP nor Melan-A, collectively indicating high specificity for the Assay (FIG. 2C).

Figure 3:
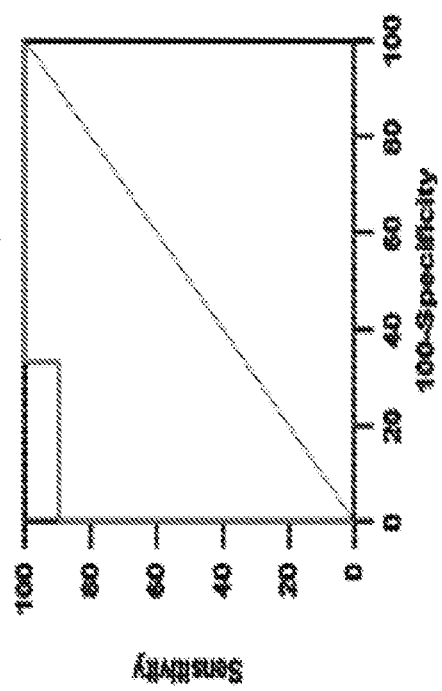
FIG. 3 provides a ROC curve demonstrating favorable Assay test characteristics. A CTC count threshold of 1.1 CTCs/mL results in Assay sensitivity of 90.0% and specificity of 91.7%.

Receiver operator characteristic (ROC) curves were generated using cell counts from the pilot and control blood studies, showing that a CTC count threshold of 1.1 CTCs/mL was able to correctly detect metastatic melanoma with a sensitivity of 90.0% and specificity of 91.7% (FIG. 3).

Disease course characteristics of the patients in the pilot study at the time of the assay CTC count (listed in order of ascending counts) are shown in Table 1. Nine of ten patients had detectable CTC counts (>1.1 CTCs/mL). NED=no evidence of disease, LN=lymph nodes, WT=wild type.

| CTCs/mL | Age | Sex | Site of Metastases | Disease Burden | BRAF mutation status | History of Chemotherapy | History of Immune Therapy |
|---|---|---|---|---|---|---|---|
| 0.7 | 60 | F | Gingiva | NED | WT | N | N |
| 1.2 | 66 | M | Subcutaneous skin and distant LN | High | WT | Y | Y |
| 1.4 | 71 | F | Bone and gallbladder | High | WT | Y | Y |

-continued

| CTCs/mL | Age | Sex | Site of Metastases | Disease Burden | BRAF mutation status | History of Chemo- therapy | History of Immune Therapy |
|---|---|---|---|---|---|---|---|
| 1.8 | 70 | F | In-transit skin | Low | WT | N | Y |
| 2 | 65 | F | Thigh | Low | WT | Y | Y |
| 3.4 | 61 | M | Lung, brain, and small bowel | NED | WT | N | N |
| 4.3 | 61 | F | Face | NED | Mutant | N | Y |
| 6.6 | 53 | F | Scalp | Low | WT | N | Y |
| 11.5 | 66 | F | Lung | Low | WT | N | Y |
| 27.1 | 38 | M | Lung, neck, and LN | High | Mutant | N | Y |

The blood samples from nine of the ten patients contained detectable CTCs (defined through the ROC curves as greater than 1.1 CTCs/mL). The median count was 2.7 CTCs/mL (range 0.7-27.1). The subjects were 70% female with a median age of 63 (range 38-71). Three subjects were considered to be without radiographic evidence of disease (no evidence of disease, NED) and four subjects were considered to have low burden of disease. Despite low burden of disease at last evaluation, these subjects were considered at high risk of recurrence. The majority of subjects had dermal, lymph node, or recurrent skin disease and four had visceral involvement (brain, lung, gallbladder, bowel, etc.).

In univariate analysis, only the presence of a BRAF mutation had a trend toward significant correlation with CTC levels (p=0.051). In contrast, none of the other factors significantly correlated with CTC levels (including age, sex, burden of disease, site of metastasis, and recent history of chemo- or immune therapy) (Table 2). Table 2 provides the results of one-way analysis of variance for single variables and linear regression model for multivariate analysis. NED=no evidence of disease, LN=lymph node, WT=wild type.

TABLE 2

| Univariate analysis | p-value |
|---|---|
| Age (<65 vs ≥65) | 0.38 |
| Sex | 0.27 |
| Site of metastasis (dermal or LN vs other viscera) | 0.13 |
| Burden of disease (NED vs low vs high) | 0.31 |
| BRAF mutation status (WT vs mutant) | 0.051 |
| History of chemotherapy | 0.28 |
| History of immune therapy | 0.47 |

| Multivariable analysis | Regression Coefficient | p-value |
|---|---|---|
| Burden of disease (NED vs low vs high) | 7.20 | 0.03 |
| BRAF mutation status (WT vs mutant) | 8.02 | 0.10 |
| History of chemotherapy | -10.94 | 0.04 |

A linear regression model taking into consideration burden of disease, BRAF mutation status, and history of chemotherapy treatment was constructed. This multivariate analysis revealed that higher CTC counts were significantly correlated with greater burden of disease (p=0.03), while, in contrast, lower CTC counts significantly correlated with recent history of cytotoxic chemotherapy (p=0.04). BRAF mutation status was not found to be associated with higher CTC levels by multivariable analysis.

The clinical status following completion of the Assay was obtained for each patient. The odds ratio (OR) of developing recurrence at six months if the CTC level was ≥2 CTCs/mL was 6.0 (95% CI: 0.4-101.6, p=0.21). Although the sample size is small, these results suggested 80% sensitivity and 60% specificity for prediction of progression of disease with the Assay.

Figure 6A:
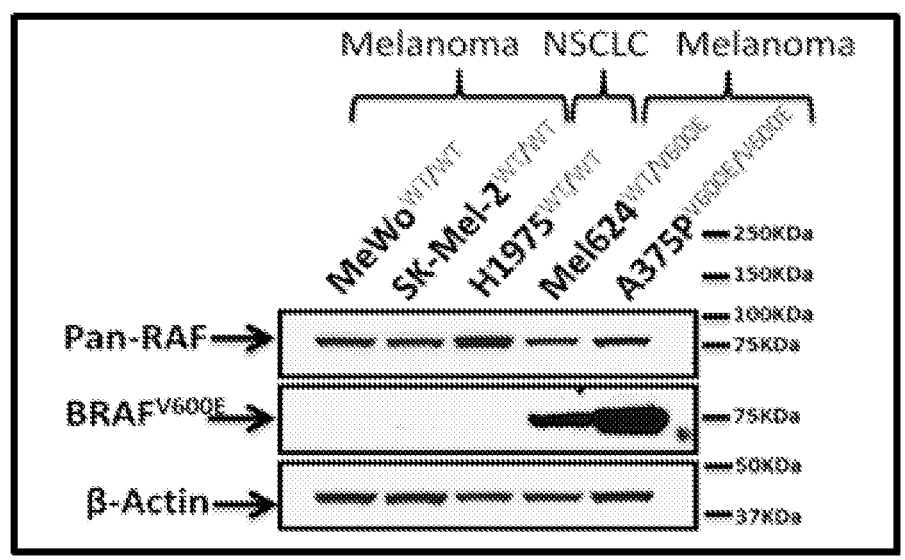
FIGS. 6A-6C provide the characterization of the BRAF status of melanoma cell lines.
Figure 6B:
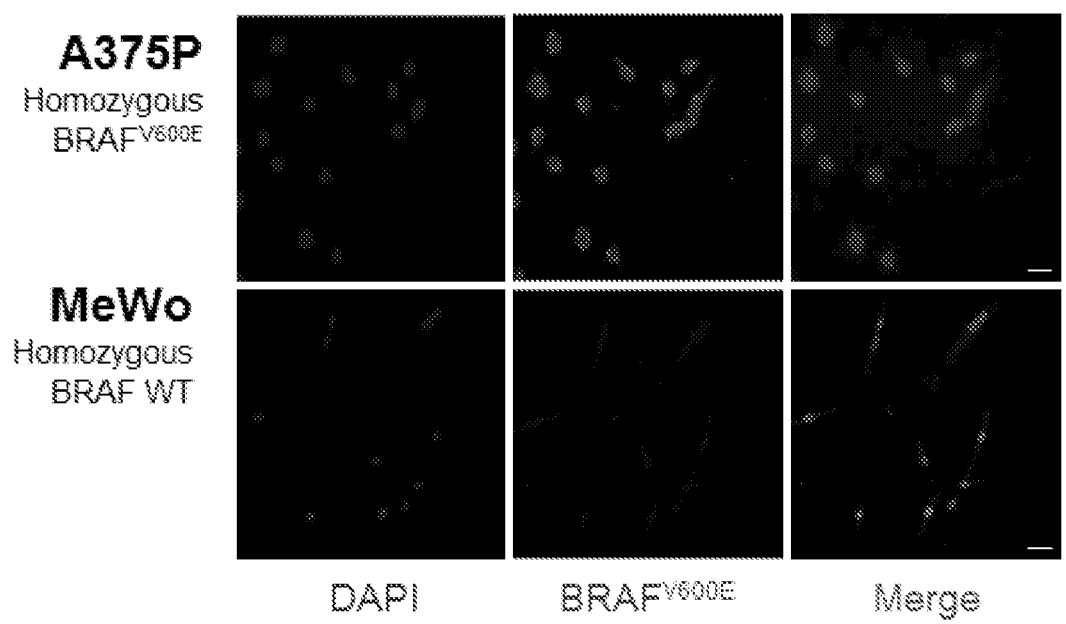
Figure 6C:
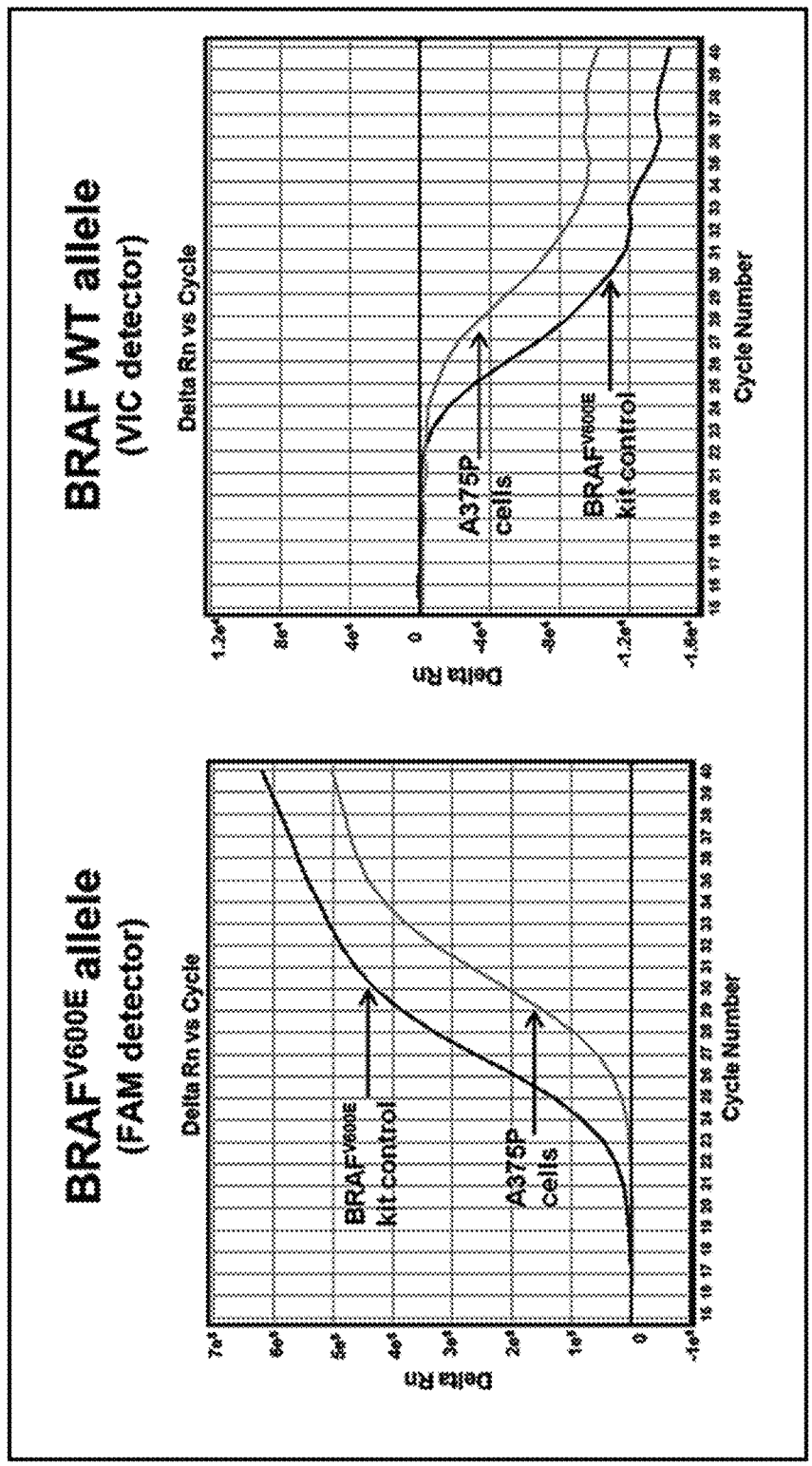

3. The Assay allows isolation of individual Melanoma Circulating Tumor Cells and characterization of their BRAF mutation status Whether CTCs identified through the Assay could be isolated and subject to additional analyses was analyzed, particularly for specific genetic mutations of therapeutic relevance for melanoma. The protocols described herein were developed utilizing capillary-based isolation of individual cells (manuscript in preparation, FIG. 4A, and FIG. 5). As described herein, melanoma cells were first tested in culture, characterizing A375P (homozygous $BRAF^{V600E}$ mutated), Me1624 (heterozygous $BRAF^{V600E}$ mutated), and MeWo (homozygous BRAF WT) cell lines by BRAF mutation status (FIG. 6). Each of these cell lines was exposed to the probe, followed by isolation of individual cells from which DNA was extracted. Whole genome amplification (WGA) was performed on the extracted DNA, followed by quantitative polymerase-chain reaction (qPCR) for the $BRAF^{V600E}$ mutation (FIG. 4B, FIGS. 7A-7D). These experiments indicated that the exposure to the probe and the resultant GFP expression did not interfere with the ability to extract DNA and successfully perform WGA of the DNA. Furthermore, the $BRAF^{V600E}$ mutation was preserved in the DNA after WGA and could be readily detected via qPCR.

As a final step, these experiments were repeated with each of the cell lines spiked into blood from healthy volunteers. Similar to previous experiments, individual cells were isolated, extracted for DNA which then underwent WGA, and then subject to qPCR analysis for BRAF status. These results indicated that the presence of control blood did not interfere with each of these steps, and did not impede the accurate determination of the BRAF mutation status (FIG. 4C, FIG. 7C).

Encouraged by the success of these experiments, the protocol was tested on blood from patients with melanoma. In each of these representative patients, the Assay identified CTCs, which were then isolated with our capillary-based procedures, and extracted DNA underwent WGA. For each of the patients, the results of the qPCR analysis for BRAF mutation in the DNA extracted from CTCs matched the BRAF mutation status of the primary tumor (FIG. 4D, FIG. 7D).

C. Discussion

To our knowledge, this study is the first to describe a telomerase-based approach to detecting melanoma CTCs. The feasibility of this Assay was assessed in through these pre-clinical studies and in a pilot study of melanoma patients. The adenoviral-based probe was found to be highly sensitive (91.8%) and specific (99.9%) for melanoma cells and its efficacy was not affected by BRAF mutation status. The melanoma-origin of the detected cells in culture and in samples from patients was confirmed via co-staining for anti-Melan-A, thus distinguishing melanoma cells (DAPI+/GFP+/Melan A+) from the surrounding WBCs (DAPI+/GFP−/Melan A−) (FIG. 2C). The GFP expression in cancer cells exposed to the probe enabled analysis and optimization via flow cytometry techniques and quantification via semi-automated computer image analysis. Finally, we applied the Assay to patients with metastatic melanoma, which successfully detected CTCs in the majority of patients tested. These results enabled the calculation of ROC curve indicating detection of CTCs with a sensitivity of 90.0% and specificity of 91.7%.

A number of observations merit comment. CTCs were identified in patients with both BRAF WT and BRAF mutant alleles, but in the univariate analysis, BRAF mutation showed a trend toward association with higher CTC counts (p=0.051). This may reflect the biological aggressiveness of the disease, but serial analysis for CTCs in patients with BRAF mutations may also help track responsiveness to BRAF inhibitors [Long G V, et al. J Clin Oncol. 2011; 29(10):1239-1246 and Chapman P B, et al. N Engl J Med. 2011; 364(26):2507-2516]. Increased burden of disease was found to be associated with increased CTCs levels (p=0.03). However, history of recent cytotoxic chemotherapy was associated with decreased CTC levels (p=0.04). This may be due to systemic chemotherapy clearing the serum of CTCs in vivo or impairing cell viability and adversely affecting the ability of cancer cells to express fluorescence, which we have observed in in vitro experiments (data not shown). Additional studies would be needed to determine how much time after chemotherapy would be ideal to perform the Assay and/or if the assay's ability to only detect live cancer cells proves to be advantageous for determining prognosis in the setting of chemotherapy administration. In contrast, recent history of immunotherapy did not appear to affect CTC counts, perhaps due to the indirect or delayed mechanism of action by immunomodulation. Intriguingly, the six month recurrence data in these patients suggest that a CTC threshold of 2 CTCs/mL might predict progression of disease with an OR of 6.0 (although due to small sample size, this OR was not statistically significant with p=0.21).

The feasibility of cell isolation and BRAF mutation analysis in melanoma CTCs using capillary-based isolation has been demonstrated herein. The ability to identify individual cancer cells with precision, followed by the techniques described herein for isolating and characterizing the amplified DNA may thus provide a breakthrough technique. Future efforts could include next generation or whole genome sequencing of CTCs. In contrast, previous efforts to conduct genetic analysis using surface marker-based isolation methods were either limited by inability to confirm intact cells prior to analysis or were associated with suboptimal PCR results [Sakaizawa K, et al., Br J Cancer. 2012; 106(5):939-946 and Chiu C G, et al. Genome-wide characterization of circulating tumor cells identifies novel prognostic genomic alterations in systemic melanoma metastasis. Clin Chem. 2014 June; 60(6):873-85. In the experiments described herein using control blood spiked with melanoma cells as well as in patient samples, the DNA amplified from isolated cells were found to have BRAF$^{V600E}$ mutation status that match the parental cell line or tumor of origin. Continual refinement of the Assay and genetic analysis methods described here may ultimately lead to better risk stratification, monitoring of disease status and progression, detection of newly acquired genetic mutations, and responsiveness to targeted therapy for patients.

Example 2—Constructions of Illustrative Adenoviral Vector System

The fluorescent marker gene pCherryPicker was retrieved from plasmid obtained from Clontech Laboratories (other commercial sources may be selected) and cloned into an intermediate expression plasmid downstream of a chicken beta actin promoter. The fragment of CB7-pCherryPicker-was subsequently removed and to replace EGFP in an hTERT promoter driven EGFP expression cassette in pShuttle (Clontech). A synthetic fragment carrying human Ad5 E1A, IRES and E1b plus polyA signal derived from bovine growth hormone (bGH) was subsequently inserted into the above modified pShuttle plasmid in between the hTERT and CB7 promoters.

The final shuttle plasmid encodes two expression cassettes, one with E1a and E1b coexpression regulated by IRES and under the control of hTERT promoter and the other carries a reporter (pCherryPicker) with expression under the control of CB7 promoter. The dual promoters controlled expression cassettes were retrieved from the shuttle plasmid by I-Ceu-I and PI-SceI digestion and subcloned into the E1 region of an E1 deleted Ad5 genome containing plasmid backbone. The vector genome flanked by 2 PacI sites was retrieved and the fragment used for Ad vector production by transfection in 293 cells, which is performed using published methods to afford a recombinant adenoviral particle in which the two expression cassettes are packaged between the adenovirus ITRs and within the adenovirus capsid.

U.S. Provisional Patent Application No. 62/060,219, filed Oct. 6, 2014 and all publications cited in this specification are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A method useful for isolating live circulating melanoma tumor cells, said method comprising
   (a) combining ex vivo a test sample from blood of a melanoma patient suspected of having circulating melanoma tumor cells, an adenoviral probe system, and culture media for the cells, said adenoviral probe system comprising:
      a first replication-competent recombinant adenovirus comprising a nucleic acid sequence which comprises at least a first telomerase specific promoter which directs expression of an adenovirus E1a gene and/or E1b gene following infection of circulating tumor cells (CTC) with the first recombinant adenovirus, and a coding sequence for a first fluorescent reporter protein which is expressed in the adenovirus-infected CTC following expression of the adenovirus E1a gene and/or E1b gene;
   (b) incubating the test sample and the adenoviral probe system for a sufficient time to permit expression of the first fluorescent reporter protein,
      optionally replenishing the media; and
   (c) collecting cells expressing the first fluorescent reporter protein, whereby expression of the first fluorescent reporter protein indicates the presence of live CTC in the sample.

2. The method according to claim 1, wherein the telomerase specific promoter is selected from the group consisting of a human telomerase reverse transcriptase (hTERT) promoter, a human telomerase RNA (hTR) promoter, and a human telomerase RNA gene (hTERC) promoter.

3. The method according to claim 1, wherein the first replication-competent recombinant adenovirus further comprises a second fluorescent protein gene sequence under the control of regulatory sequences which direct expression thereof in the live CTC following expression of the E1a gene.

4. The method according to claim 1, wherein the first replication-competent recombinant adenovirus comprises a nucleic acid sequence encoding a fusion protein, said fusion-protein comprising a tumor associated cell surface marker protein and the first fluorescent reporter protein.

5. The method according to claim 4, further comprising capturing the infected CTC by a ligand specific for the tumor associated cell surface marker protein or a ligand specific for the first fluorescent reporter protein.

6. The method according to claim 5, wherein said ligand is an antibody.

7. The method according to claim 6, wherein said antibody is conjugated or bound to a magnetic bead.

8. The method of claim 4, further comprising identifying CTC using a probe for the tumor associated cell surface marker and a probe for the first fluorescent protein.

9. The method of claim 4, wherein the tumor associated cell surface marker protein is epithelial cell adhesion molecule (EpCam) and the first fluorescent reporter protein is green fluorescent protein (GFP).

10. The method according to claim 1, wherein the coding sequence for the first fluorescent reporter protein is operably linked to an expression control sequence and is in the site of a deletion in the adenovirus immediate early E3 gene region.

11. The method according to claim 1, wherein the adenoviral probe system further comprises at least a second, different recombinant adenovirus.

12. The method according to claim 1, wherein the first fluorescent reporter protein is cherry picker, and wherein the method further comprises capturing the infected CTC by a ligand which is an anti-cherry picker antibody.

13. The method of claim 12, wherein said antibody is conjugated or bound to a magnetic bead.

14. The method according to claim 1, further comprising counting the collected CTC expressing the first fluorescent reporter protein.

15. The method according to claim 1, wherein the adenoviral probe system further comprises a coding sequence for a second fluorescent reporter protein which is distinguishable from the first fluorescent reporter protein, wherein the second fluorescent reporter protein is specifically expressed in CTC, and wherein the method further comprises counting the collected CTC expressing the second fluorescent reporter protein.

16. The method of claim 1, wherein the first fluorescent reporter protein is expressed under the control of a constitutive promoter.

17. The method of claim 1, further comprising detecting cell size of the CTC expressing the first fluorescent reporter protein in step (c).

18. The method of claim 1, further comprising measuring fluorescence intensity of the expressed first fluorescent reporter protein in step (c).

19. The method of claim 1, further comprising
(d) combining ex vivo a control sample from blood of a healthy subject, the adenoviral probe system, and the culture media for the cells;
(e) incubating the control sample and the adenoviral probe system for the time of step (b),
optionally replenishing the media as in step (b);
(f) detecting cell size of cells from the blood of the healthy subject expressing the first fluorescent reporter protein after step (e) and fluorescence intensity of the expressed fluorescent reporter protein to establish background levels of cell size and fluorescence intensity;
(g) detecting cell size of the cells from the melanoma patient collected in step (c) and fluorescence intensity of the first fluorescent reporter protein expressed in the collected cells; and
(h) counting the cells from the melanoma patient collected in step (c) when the cells do not have a cell size or a fluorescence intensity above the background levels determined in step (f), whereby the cell count indicates the live CTC level in the sample.

20. The method according to claim 1, further comprising
(d) analyzing the live CTC from step (c) for a selected tumor associated mutation.

21. A method for tracking resistance of a targeted therapy comprising:
(a) combining ex vivo a test sample from blood of a melanoma patient suspected of having circulating tumor cells (CTC) and who has been treated with a targeted therapy, an adenoviral probe system, and culture media for the cells, said adenoviral probe system comprising:
a first replication-competent recombinant adenovirus comprising a nucleic acid sequence which comprises at least a first telomerase specific promoter which directs expression of an adenovirus E1a gene and/or E1b gene following infection of CTC with the first recombinant adenovirus, and a coding sequence for a first fluorescent reporter protein which is expressed in the infected CTC following expression of the adenovirus E1a gene and/or E1b gene;
(b) incubating the test sample and the adenoviral probe system for a sufficient time to permit infection of CTC with the adenoviral probe system and expression of the first fluorescent reporter protein in the CTC,
optionally replenishing the media;
(c) collecting the CTC expressing the first reporter protein, whereby expression of the first reporter protein indicates the presence of live CTC in the sample; and
(d) counting the CTC expressing the first fluorescent protein, whereby the presence of a level of live CTC above a control CTC count threshold indicates resistance to the targeted therapy.

22. The method of claim 21, wherein the control CTC count threshold is determined using a blood sample from a healthy subject.

23. The method of claim 21, wherein the control CTC count threshold is 1.1 CTCs/mL.

\* \* \* \* \*